United States Patent [19]
Doherty et al.

[11] Patent Number: 5,132,301
[45] Date of Patent: Jul. 21, 1992

[54] SUBSTITUTED CEPHALOSPORIN SULFONES AS ANTI-INFLAMMATORY AND ANTI-DEGENERATIVE AGENTS

[75] Inventors: James B. Doherty, New Milford; Raymond A. Firestone, Westfield; Paul E. Finke, Milltown; William K. Hagmann, Westfield; Shrenik K. Shah, Metuchen; Kevan R. Thompson, Westfield, all of N.J.

[73] Assignee: Merck & Co., Inc., Rahway, N.J.

[21] Appl. No.: 471,320

[22] Filed: Jan. 29, 1990

Related U.S. Application Data

[63] Continuation of Ser. No. 930,193, Nov. 12, 1986, abandoned, which is a continuation-in-part of Ser. No. 774,425, Sep. 10, 1985, abandoned, which is a continuation-in-part of Ser. No. 490,761, May 2, 1983, abandoned.

[51] Int. Cl.$^5$ ................ C07D 501/20; A61K 31/545
[52] U.S. Cl. ..................................... 514/201; 540/221
[58] Field of Search ................ 540/222, 221; 514/201, 514/206

[56] References Cited

U.S. PATENT DOCUMENTS

| | | | |
|---|---|---|---|
| 3,936,446 | 2/1976 | Bentley et al. | 260/263 R |
| 3,976,641 | 8/1976 | Hoover et al. | 260/243 R |
| 4,107,431 | 8/1978 | Clark et al. | 544/16 |
| 4,113,591 | 9/1978 | Laundon et al. | 204/158 |
| 4,265,882 | 5/1981 | Sheenan et al. | 424/114 |
| 4,271,157 | 6/1981 | Denzel et al. | 424/246 |
| 4,272,439 | 6/1981 | Ganguly et al. | 260/245.2 R |
| 4,283,397 | 8/1981 | Hannah | 424/246 |
| 4,296,111 | 10/1981 | Beattie et al. | 424/246 |
| 4,297,488 | 10/1981 | Christensen et al. | 544/21 |
| 4,381,300 | 4/1983 | Sheehan et al. | 424/246 |
| 4,446,318 | 5/1984 | Naito et al. | 544/26 |
| 4,459,405 | 7/1984 | Hall | 544/28 |
| 4,547,371 | 10/1985 | Doherty et al. | 514/200 |
| 4,623,645 | 11/1986 | Doherty et al. | 514/200 |
| 4,637,999 | 1/1987 | Doherty et al. | 514/201 |
| 4,699,904 | 10/1987 | Doherty et al. | 514/202 |
| 4,845,088 | 7/1989 | Doherty et al. | 514/202 |

FOREIGN PATENT DOCUMENTS

| | | |
|---|---|---|
| 0124081 | 11/1984 | European Pat. Off. |
| 2534926 | 2/1974 | Fed. Rep. of Germany |
| 2927462 | 1/1981 | Fed. Rep. of Germany |
| 3015395 | 2/1978 | Japan |
| 1603212 | 11/1981 | United Kingdom |

OTHER PUBLICATIONS

Cephalosporins and Penicillins, Academic Press 1972 p. 577.
J. R. Corfield, et al., Tetrahedron Letters, No. 32, 2915 (1978).
Doherty et al., Nature, vol. 322, No. 6075, pp. 192–194 (1986).
T. E. Gunda et al., Acta Chemica Scandinavica B, p. 33 (1983).
J. C. Jaszenbernyi, et al., Acta Chimica Academiae Scientiarum Hungaricae tomers 98 (1) p. 105 (1978).
J. Medicinal Chem. v. 21, No. 2, pp. 240–242 (1978).
Yoshida et al., Chem. Pharm. Bull. 23 (11) pp. 2507–2517 (1975).

*Primary Examiner*—Nicholas S. Rizzo
*Attorney, Agent, or Firm*—Curtis C. Panzer; Hesna J. Pfeiffer

[57] ABSTRACT

New substituted cephalosporin sulfones are found to be potent elastase inhibitors and thereby useful anti-inflammatory/antidegenerative agents.

6 Claims, No Drawings

SUBSTITUTED CEPHALOSPORIN SULFONES AS ANTI-INFLAMMATORY AND ANTI-DEGENERATIVE AGENTS

This is a continuation of application Ser. No. 930,193 filed Nov. 12, 1986 now abandoned which is a continuation in part of U.S. Ser. No. 774,425 filed Sep. 10, 1985, now abandoned which was a continuation in part of U.S. Ser. No. 490,761 filed May 2, 1983, now abandoned.

BACKGROUND OF THE INVENTION

We have found that sulfones of a group of new substituted cephalosporins are potent elastase inhibitors and therefore are useful anti-inflammatory/antidegenerative agents.

Proteases from granulocytes and macrophages have been reported to be responsible for the chronic tissue destruction mechanisms associated with inflammation, including rheumatoid arthritis and emphysema. Accordingly, specific and selective inhibitors of these proteases are candidates for potent anti-inflammatory agents useful in the treatment of inflammatory conditions resulting in connective tissue destruction, e.g. rheumatoid arthritis, emphysema, bronchial inflammation, osteoarthritis, spondylitis, lupus, psoriasis and acute respiratory distress syndrome.

The role of proteases from granulocytes, leukocytes or macrophages are related to a rapid series of events which occurs during the progression of an inflammatory condition:

(1) There is a rapid production of prostaglandins (PG) and related compounds synthesized from arachidonic acid. This PG synthesis has been shown to be inhibited by aspirin-related nonsteroidal anti-inflammatory agents including indomethacin and phenylbutazone. There is some evidence that protease inhibitors prevent PG production;

(2) There is also a change in vascular permeability which causes a leakage of fluid into the inflamed site and the resulting edema is generally used as a marker for measuring the degree of inflammation. This process has been found to be induced by the proteolytic or peptide cleaving activity of proteases, especially those contained in the granulocyte, and thereby can be inhibited by various synthetic protease inhibitors, for example, N-acyl benzisothiazolones and the respective 1,1-dioxides. Morris Zimmerman et al., *J. Biol. Chem.*, 255, 9848 (1980); and (3) There is an appearance and/or presence of lymphoid cells, especially macrophages and polymorphonuclear leukocytes (PMN). It has been known that a variety of proteases are released from the macrophages and PMN, further indicating that the proteases do play an important role in inflammation.

In general, proteases are an important family of enzymes within the peptide bond cleaving enzymes whose members are essential to a variety of normal biological activities, such as digestion, formation and dissolution of blood clots, the formation of active forms of hormones, the immune reaction to foreign cells and organisms, etc., and in pathological conditions such as the degradation of structural proteins at the articular cartilage/pannus junction in rheumatoid arthritis etc.

Elastase is one of the proteases. It is an enzyme capable of hydrolyzing the connective tissue component elastin, a property not contained by the bulk of the proteases present in mammals. It acts on a protein's nonterminal bonds which are adjacent to an aliphatic amino acid. Neutrophil elastase is of particular interest because it has the broadest spectrum of activity against natural connective tissue substrates. In particular, the elastase of the granulocyte is important because, as described above, granulocytes participate in acute inflammation and in acute exacerbation of chronic forms of inflammation which characterize many clinically important inflammatory diseases Proteases may be inactivated by inhibitors which block the active site of the enzyme by binding tightly thereto. Naturally occurring protease inhibitors form part of the control or defense mechanisms that are crucial to the well-being of an organism. Without these control mechanisms, the proteases would destroy any protein within reach. The naturally occurring enzyme inhibitors have been shown to have appropriate configurations which allow them to bind tightly to the enzyme. This configuration is part of the reason that inhibitors bind to the enzyme so tightly (see Stroud, "A Family of Protein-Cutting Proteins" *Sci. Am.* July 1974, pp. 74-88). For example, one of the natural inhibitors, $\alpha_1$-Antitrypsin, is a glycoprotein contained in human serum that has a wide inhibitory spectrum covering, among other enzymes, elastase both from the pancreas and the PMN. This inhibitor is hydrolyzed by the proteases to form a stable acyl enzyme in which the active site is no longer available. Marked reduction in serum $\alpha_1$-antitrypsin, either genetic or due to oxidants, has been associated with pulmonary emphysema which is a disease characterized by a progressive loss of lung elasticity and resulting respiratory difficulty. It has been reported that this loss of lung elasticity is caused by the progressive, uncontrolled proteolysis or destruction of the structure of lung tissue by proteases such as elastase released from leukocytes. J. C. Powers, *TIBS*, 211 (1976).

Rheumatoid arthritis is characterized by a progressive destruction of articular cartilage both on the free surface bordering the joint space and at the erosion front built up by synovial tissue toward the cartilage. This destruction process, in turn, is attributed to the protein-cutting enzyme elastase which is a neutral protease present in human granulocytes. This conclusion has been supported by the following observations:

(1) Recent histochemical investigations showed the accumulation of granulocytes at the cartilage/pannus junction in rheumatoid arthritis; and (2) a recent investigation of mechanical behavior of cartilage in response to attack by purified elastase demonstrated the direct participation of granulocyte enzymes. especially elastase, in rheumatoid cartilage destruction. H. Menninger et al., in *Biological Functions of proteinases*, H. Holzer and H. Tschesche, eds. Springer-Verlag, Berlin, Heidelburg, N.Y. pp. 196-206, 1979.

Accordingly, an object of this invention is to discover new protease inhibitors, especially elastase inhibitors, useful for controlling tissue damage and various inflammatory or degenerative conditions mediated by proteases particularly elastase.

Another object of the present invention is to provide pharmaceutical compositions for administering the active substituted cephalosporin sulfones as protease inhibitors.

Still a further object of this invention is to provide a method of controlling inflammatory conditions by administering a sufficient amount of one or more of the active, substituted cephalosporin sulfones in a mammalian species in need of such treatment.

DETAILED DESCRIPTION OF THE INVENTION

This invention relates to new cephalosporin sulfones as potent elastase inhibitors useful in the prevention, control and treatment of inflammatory conditions especially arthritis and emphysema.

Some of the cephalosporin free acids are known antibiotics which have been described in U.S. Pat. No. 4,297,488 issued Oct. 27, 1981.

The structural formula of the cephalosporin sulfones of the present invention are represented as follows:

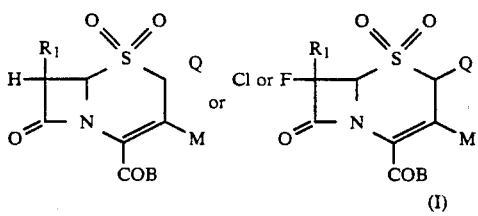

(I)

wherein M is:
(1) trifluoromethyl;
(2) chloro or fluoro;
(3) —COOH;
(4) —CHO; or
(5) —CH$_2$A wherein A represents
 (a) hydrogen;
 (b) halo;
 (c) hydroxy;
 (d) alkoxy;
 (e) aryloxy;
 (f) aralkyloxy;
 (g) unsubstituted or substituted mercapto;
 (h) acylthio;
 (i) acyloxy especially alkanoyloxy or arylcarbonyloxy such as acetoxy, benzyloxycarbonyloxy, benzoyloxy; and succinoyloxy; substituted or unsubstituted carbamoyl, thiocarbamoyl and N-alkyl or N,N-dialkyl derivatives thereof;
 (j) a quaternary ammonium group, for example, —N$^{\oplus}$H$_3$, —N$^{\oplus}$HE$_2$, or —N$^{\oplus}$E$^3$ where E represents loweralkyl, aryl or aralkyl;
 (k) unsubstituted or substituted amino or amido group especially —NH$_2$, —CONH$_2$ and N-alkyl or N,N-dialkyl derivatives thereof;
 (l) R—SO— wherein R is C$_{1-16}$alkyl or C$_{6-10}$aryl: or
 (m) R—SO$^2$—;
(6) —CH=CHR.

Thus, CH$_2$A can be a halomethyl such as chloromethyl, bromomethyl or fluoromethyl.

When CH$_2$A is a substituted hydroxy or substituted mercapto group, it can be shown by the formula

—CH$_2$ZR$_5$ where Z is oxygen or sulfur, and R$_5$ is an acyl group; a straight chain or branched chain loweralkyl, alkenyl or alkynyl group; an aryl group; an aralkyl group; or a heterocyclic group such as heteroaryl, heterocycloalkyl e.g., 1,3-dioxacyclohex-4-yl, piperidino, morpholino, oxacyclopropyl, pyrrolidino, tetrazolo, benzothiazolo, imidazolidino, pyrazolidino, and piperazino; or heterocycloalkenyl such as pyrrolino, 2-imidazolino, 3-pyrazolino or isoindolino. These groups can be unsubstituted or can be substituted by radicals such as alkyl, alkoxy, halo, cyano, carboxy, carbamoyl, azido,, sulfo, amino,, substituted amino, haloalkyl, carboxyalkyl, carbamoylalkyl, N-substituted carbamoylalkyl, guanidino, N-substituted guanidino, guanidoalkyl, sulfamyl, substituted sulfamyl, and the like. Representative of the CH$_2$A groups are methoxymethyl, n-propoxymethyl, methylthiomethyl, acetoxymethyl, propionyloxymethyl benzoyloxymethyl (p-chlorobenzoyl)oxymethyl, succinoyloxymethyl, (p-methylbenzoyl)oxymethyl, pivaloyloxymethyl, (1-adamantyl)-carboxymethyl, butanoyloxymethyl, carbamoyloxymethyl, (N-methylcarbamoyl)oxymethyl, (N-ethylcarbamoyl)oxymethyl, [N-(2-chloroethyl) carbamoyl]oxymethyl, (N-phenylcarbamoyl)oxymethyl, [N-(carboxymethyl)carbamoyl]oxymethyl, (N-p-sulfophenyl-carbamoyl)oxymethyl, p-carboxymethylphenyl-carbamoyloxymethyl, methoxycarbonyloxymethyl, isobutanoyloxymethyl, cyclobutylcarbonyloxymethyl, carbamoylthiomethyl, (ethoxythiocarbonyl)thiomethyl, (n-propoxythiocarbonyl) thiomethyl, (cyclopentanoxythiocarbonyl)thiomethyl, methylthiomethyl, N,N-diethylthiocarbamoylthiomethyl, N-methylpiperazinium-1-thiocarbonylthiomethyl, N,N-dimethylpiperazinyl-1-thiocarbonylthiomethyl, 2-furoylthiomethyl, isothiouronioummethyl, (5-methyl-1,3,4-thiadiazol-2-yl)thiomethyl, p-tolylsulfonylthiomethyl, 2-benzothiazolothiomethyl, mesyloxymethyl, 1-methyl-1,2,3,4-tetrazolyl-5-thiomethyl, tosyloxymethyl, sulfamoyloxymethyl, 1-naphthoyloxymethyl, 2-furylacetoxymethyl, cinnamoyloxymethyl, p-hydroxycinnamoyloxymethyl, p-sulfocinnamoyloxymethyl and 1R:2S-epoxypropylphosphonyloxymethyl.

Alternatively, when CH$_2$A is hydroxymethyl, the cephalosporin can also exist as the lactone which is formed by internal esterification with the adjacent carboxy group.

The substituent CH$_2$A can also be a group of the general formula

—CH$_2$Y$_1$ wherein Y$_1$ represents amino or substituted amino including nitrogen heterocycles and substituted heterocyclic groups as described for R$_5$. Y$_1$ may also be nitrogen which is part of the heterocyclic system as shown below.

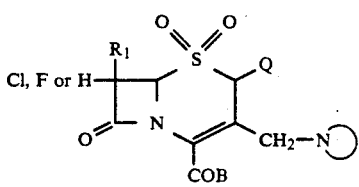

Examples of such groups that might be mentioned are aminomethyl, acetamidomethyl, carbamoylaminomethyl, N,N-dimethylaminomethyl, N-(2-chloroethyl)-aminomethyl, 5-cyano-triazol-1-yl-methyl, 4-methoxy-carbonyltriazol-1-yl-methyl.

When A is amino the cephalosporin compound can also exist as the lactam formed by loss of water with the adjacent carboxy group.

Representative of the quaternary ammonium groups representing A that might be mentioned are pyridinium, 3-methylpyridinium, 4-methylpyridinium, 3-chloropyridinium, 3-bromopyridinium, 3-iodopyrinium, 4-carbamoylpyridinium, 4-(N-hydroxymethylcarbamoyl)pyridinium, 4-(N-cyanocarbamoyl)pyridinium, 4-carboxymethylpyridinium, 4-hydroxymethylpyridinium, 4-trifluoromethyl-pyridinium, quinolinium, picolinium and lutidinium.

When A is mercapto, it may be —SH,

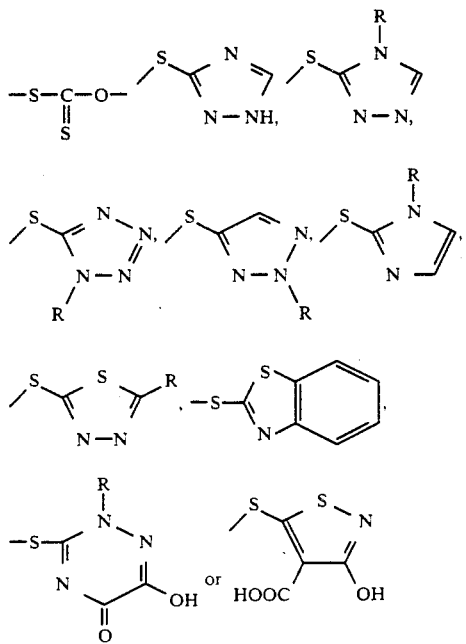

alkyl, alkylthio, arylthio, aralkylthio or heterocyclothio, wherein R represents $C_{1-16}$ loweralkyl, $C_{6-10}$ aryl or $CH_2COOH$.

The preferred groups representing A are (a) hydrogen; (b) halo; (c) hydroxy; (d) alkoxy; (e) aryloxy; (f) aralkyloxy; (g) substituted or unsubstituted mercapto especially

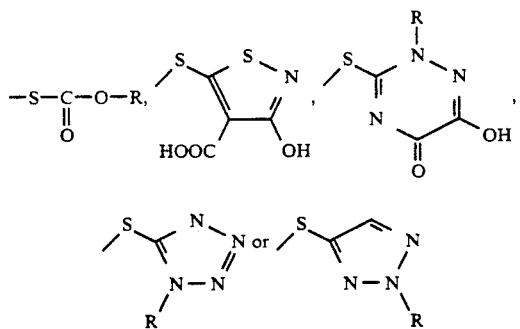

(h) acylthio; or (i) acyloxy. The acyl group can be a loweralkanoyl group of 2-6 carbon atoms such as acetyl, —$COC_2H_5$ or —$COC_3H_7$, carbamoyl, or thiocarbamoyl and N-alkyl or N,N-dialkyl derivatives thereof. The alkyl group of the foregoing substituents contains 1-10 carbon atoms and may be further substituted by radicals such as alkoxy, halo, amino, cyano, carboxy, sulfo, and the like.

More preferably, A is (a) alkanoyloxy especially

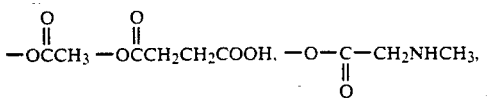

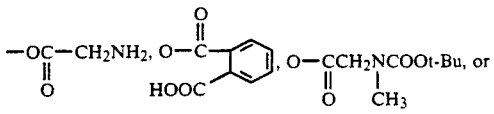

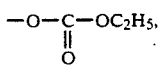

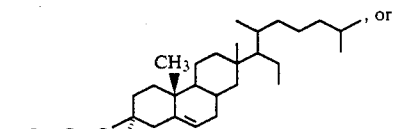

—O—C—O—$(CH_2)_{21}CH_3$;
‖
O (b) alkoxy especially methoxy, ethoxy or i- or n-propyloxy;
(c) halo;
(d) hydrogen;
(e) hydroxy;
(f) substituted or unsubstituted mercapto; or
(g) carbamoyloxy, especially

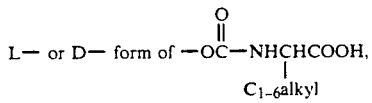

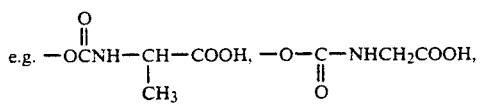

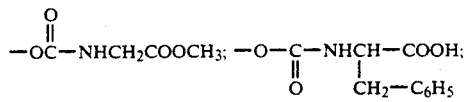

(h) —$SOCH_3$ or —SO—$C_6H_5$;
(i) —$SO_2CH_3$ or —$SO_2C_6H_5$;

The substituent $R_1$ in formula (I) above is
(a) hydrogen;
(b) hydroxy;
(c) mercapto;
(d) substituted oxy;
(e) substituted thio;
(f) hydrocarbyl or substituted hydrocarbyl group;
(g) cyano;
(h) carbonyl or thiocarbonyl containing substituents bonded by said carbonyl or thiocarbonyl radical;
(i) halo;
(j) phosphono or a substituted phosphono group;

The oxy or thio substituent represented by $R_1$ in formula (I) can be a substituted hydroxy or mercapto group such as —XR'₁ wherein X is oxygen or sulfur and R'₁ is a hydrocarbyl group, preferably a straight or branched loweralkyl group of 1-6 carbon atoms, a straight or branched chain loweralkenyl or loweralkynyl group of 3-6 carbon atoms, a monocyclic aryl group such as phenyl, furyl, pyrryl and pyridyl, or an aralkyl group such as benzyl. These alkyl, alkenyl, alkynyl, aryl or aralkyl groups can be substituted with groups such as hydroxy, halo, nitro, amino, carboxy, thio, and the like Other specific substituents represented by R₁ that might be mentioned are groups of the formula —OAc, —SAc, —SO₃H, —SO₂NH₂, —SO₂R₂, —SO₂NR₃R₄, —OCOOR₂, —SOR₂, —OCOSR₂, —OCONR₃R₄, the like wherein Ac represents an acyl group such as a formyl or lower-alkanoyl, R₃ and R₄ represent hydrogen, lower-alkyl, acyl and loweralkoxy, and R₂ represents loweralkyl, haloloweralkyl, aryl, aralkyl and substituted derivatives of such groups.

When R₁ is hydrocarbyl it can be straight or branched loweralkyl, straight or branched lower-alkenyl, loweralkynyl, aralkyl, cycloalkyl, a monocyclic aryl group, or a monocyclic heterocyclic group which can also be substituted with one or more groups such as halo, hydroxy, alkoxy, amino, nitro, sulfonyl, sulfamoyl, acyloxy, carbamoyloxy, carboxy, carboxamido and N-substituted carboxamido. Representative examples of such groups are $C_{1-6}$ alkyl such as methyl, trifluoromethyl, ethyl, n-propyl, isopropyl, t-butyl; $C_{2-6}$ alkenyl especially allyl, α-butenyl; $C_{2-6}$ such as ethynyl and methylethynyl; loweraralkyl such as benzyl, p-methoxybenzyl, phenethyl; phenyl, p-aminophenyl; cyclopropyl, cyclopentyl and 4-hydroxycyclohexyl;

R₁ in formula (I) above may also represent cyano or a group of the general formula

wherein X' is oxygen or sulfur, and R" is hydrogen, halo, hydroxy, mercapto, amino, substituted amino, alkyl, aryl, aralkyl, aralkoxy such as benzyloxy, alkoxy or aryloxy such as phenoxy, pyrroloxy, furyloxy, and thienyloxy, alkylthio or arylthio. Examples of these substituents are —COOH, —CSSH, —COR₂, —COOR₂, —COSR₂, —CSSR₂, —CONH₂, —CSNH₂, —CSR₂, —CONHR₂, —CSNH, —CONR₃R₄ and —CSNR₃R₄ wherein R₂ represents a straight or branched chain alkyl group of 1-6 carbon atoms and R₃ and R₄ represent hydrogen or R₂;

Finally, the substituent R₁ in formula (I) represents phosphono or a metal or ammonium salt thereof, or a substituted phosphono group of the formula:

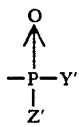

where Y' and Z' are the same or different and represent

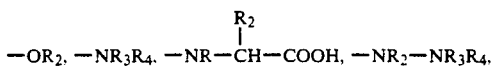

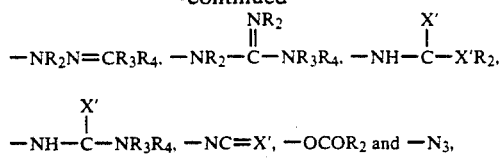

where R₂ represents hydrogen or a hydrocarbyl radical, R₃ and R₄ represent hydrogen, hydrocarbyl, alkoxy or an acyl radical, and X. represents oxygen or sulfur.

Preferably, R₁ is
(1) hydroxy;
(2) OR₁, where R₁, represents hydrocarbyl group;
(3) $C_{1-6}$alkylthio;
(4) $C_{1-6}$ alkylsulfinyl;
(5) $C_{1-6}$ alkylsulfonyl;
(6) halo such as fluoro, chloro, bromo or iodo; or;
(7) hydrogen; or
(9) $C_{1-6}$alkyl.

Even more preferably, R₁ is
(1) $C_{1-3}$alkyl;
(2) hydroxy;
(3) OR₁ where R₁' is
  (a) $C_{1-6}$ alkyl especially methyl, ethyl, n-propyl;
  (b) —C₆H₅;
  (c) —CH₂CH₂C₆H₅; or (d) 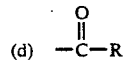

where R represents hydrogen, $C_{1-6}$alkyl, phenyl, substituted or unsubstituted benzyl, or $C_{1-6}$alkylamino such as CH₃NH—, C₂H₅NH—;
(4) halo especially Cl or F; or
(5) —SO₂R.

B of Formula (I) above represents OB1, or NB₂B₃ wherein B₁ and B₂ independently are:
(a) straight or branched chain alkyl having from 1 to 20 carbon atoms, ethyl, isopropyl, t-butyl, pentyl or hexyl;
(b) aryl having from 6 to 10 carbon atoms;
(c) cycloalkyl having from 3 to 8 carbon atoms;
(d) alkenyl having from 2 to 20 carbon atoms;
(e) cycloalkenyl having from 5 to 8 carbon atoms;
(f) alkynyl having from 2 to 20 carbon atoms;
(g) alkoxy having from 1 to 10 carbon atoms;
(h) aralkyl, alkaryl, aralkenyl, aralkynyl, alkenylaryl or alkynylaryl wherein alkyl, aryl, alkenyl and alkynyl are as previously defined;
(i) loweralkenylalkyl;
(j) alkanoylalkyl;
(k) alkanoyloxyalkyl;
(l) alkoxyalkyl;
(m) alkanoyloxy;
(n) a heterocyclic group including heterocyclic alkyl or heterocyclic alkenyl.

The above groups (a)-(n) can be unsubstituted or can be substituted by radicals such as alkyl, hydroxy, alkoxy, halo, nitro, mercapto, amino, substituted amino, cyano, carboxy, sulfoamino, carbamoyl, carbamoyloxy, sulfonyl, sulfinyl, sulfamoyl, azido, amino, substituted amino, carboxamido or N-substituted carboxamido;

B₃ is hydrogen or B₁; and

B₂ and B₃ may join together and form part of the heterocyclic group —N⟩ e.g.:

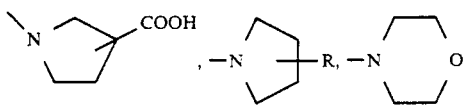

or the like.

Representative examples of such groups are $C_{1-6}$alkyl especially methyl, ethyl or t-butyl, allyl, 3-butenyl methoxyethyl, benzyl, p-carbomethoxybenzyl, m-carbomethoxybenzyl, p-sulfonylbenzyl, m-fluorobenzyl, o,p-dinitrobenzyl, o,p-dichlorobenzyl, p-methylbenzyl, m-methoxybenzyl, o-methylthiobenzyl, benzhydryl, —$CH_2COOH$, —$CH_2COOt$—Bu, $CH_2CH_2CH_2COOCH_3$, —$CH_3COOC_2H_5$, and the like.

Preferably, $B_1$ and $B_2$ independently are substituted or unsubstituted (1) aralkyl;
(2) aryl;
(3) straight or branched loweralkyl;
(4) straight or branched loweralkenyl;
(5) cycloalkyl;
(6) alkanoyloxyloweralkyl;
(7) alkanoylloweralkyl;
(8) alkoxyloweralkyl; or
(9) haloalkyl;

$B_3$ is hydrogen or $B_1$; and $B_2$ and $B_3$ may join together and form part of the heterocyclic group as defined previously;

Even more preferably, $B_1$ and $B_2$ independently are substituted or unsubstituted (1) benzyl;
(2) methyl;
(3) t-butyl;
(4) —$CH_2CH_2CH=CH_2$ or $CH_2$—$CH=C(CH_3)_2$;
(5) —$CH_2COOH$;
(6) alkanoyloxymethyl; or
(7) alkanoylmethyl;

$B_2$ is hydrogen or $B_1$; and $B_2$ and $B_3$ may join together and form part of the heterocyclic group selected from a group consisting of:

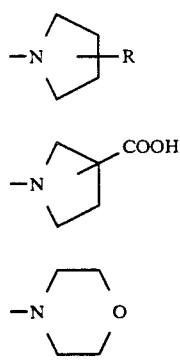

Q in formula (I) represents (1) hydrogen;
(2) $C_{1-6}$ alkyl especially methyl, ethyl, isopropyl, n-pentyl or n-hexyl;
(3) halo $C_{1-6}$alkyl especially chloro or fluoro $C_{1-6}$alkyl; or
(4) hydroxy $C_{1-6}$alkyl;
(5) methylene or substituted methylene especially $C_{1-6}$ alkylmethylene, unsubstituted or substituted phenylmethylene phenylthiomethylene. phenylsulfinylmethylene or phenyl sulfonylmethylene;
(6) $C_{1-6}$alkoxy $C_{1-6}$ alkyl;
(7) aralkyl especially unsubstituted or substituted benzyl or phenethyl;
(8) unsubstituted or substituted phenylthio $C_{1-6}$alkyl, phenylsulfonyl $C_{1-6}$;
(9) unsubstituted or substituted phenoxy $C_{1-6}$alkyl; or
(10) unsubstituted or substituted phenylamino $C_{1-6}$alkyl.

Preferably Q is
(1) hydrogen;
(2) $C_{1-6}$alkyl;
(3) substituted or unsubstituted methylene;
(4) unsubstituted or substituted phenylthio $C_{1-6}$alkyl or phenylsulfonyl $C_{1-6}$alkyl; or
(5) aralkyl.

Even more preferably, Q is
(1) hydrogen;
(2) methyl, ethyl or i-or n-propyl;
(3) methylene; or
(4) phenylthiomethyl or phenylsulfonyl methyl.

The cephalosporin sulfone esters of structural formula (I) where $OB_1$ is other than hydroxy can be prepared from the corresponding acid according to conventional methods of esterification. For example, (1) A compound of formula (I) is treated with a lower alkanol, a substituted or unsubstituted benzyl alcohol, or a substituted or unsubstituted benzhydrol (diphenylmethanol) in the presence of a catalyst and any one or a combination of those illustrated below in Table I:

TABLE I

Catalysts for Esterification (1) Hydrochloric acid or hydrobromic acid
(2) Sulfuric acid
(3) $C_{1-3}$alkanoic acid e.g. acetic acid
(4) Phosphoric acid
(5) Trifluoroacetic acid or anhydride
(6) Trichloroacetic acid
(7) p-Toluenesulfonic acid or other arylsulfonic acids
(8) Acidic ion-exchange resins with calcium sulfate
(9) Polymer-protected aluminum chloride, e.g., a complex between anhydrous aluminum chloride and polystyrene-divinyl benzene copolymer diphenylphosphitepyridine
(10) A Lewis acid such as boron trifluoride
(11) Aromatic sulfonylchloride-pyridine, e.g., p-toluenesulfonylchloride
(12) triphenylphosphine ditriflate
(13) dicyclohexylcarbodiimide (DCCD)
(14) $\beta$-trichloromethyl-$\beta$-pro-piolactone
(15) N,N'-carbonyldimidazole
(16) triphenylphosphine diethylazodicarbonylate
(17) 6-chlorobenzensulfonyloxybenzotriazole
(18) 1-methyl-2-halopyridinium iodide-tertiary amine (e.g., triethylamine).

at from about 0° to about 150° C. with or without refluxing until the esterification is substantially complete. Optionally a solvent may be used to facilitate the reaction. The common solvents used are benzene, toluene, xylene, sulfolane-xylene, diethylether, tetrahydrofuran, 1,2-dimethoxyethane, dioxane and the like;

(2) A compound of formula (I) is converted to an acid halide such as acid chloride or bromide via treatment with a halogenating agent such as thionyl chloride, phosphorus penta- or oxychloride followed by reaction with an appropriate alcohol; and (3) Other methods such as alkylation of carboxylate salts (e.g., $K^+$, $Na^+$, $Ca^{++}$, $Ag^+$, $Cu^+$, tetraalkylammonium $R_4N^+$, and $Hg^{++}$ salts) of formula (I) with alkyl halides, for example, benzylchloride, benzhydryl chloride; reaction with alkyl isoureas; treatment with diazomethane or diazophenylmethane ($C_6H_5CHN_2$); alcoholysis of anhydride derived from the cephalosporin acid corresponding to formula (I); transesterification with t-butyl esters or isopropenylacetate; and the like may also be used. These methods are disclosed in Saul Patai, editor, *The Chemistry of Functional Groups*. Supplement B, *The Chemistry of Acid Derivatives.* pp. 411-436, John Wiley & Sons, Chichester-New York-Brisbane-Toronto, 1979, and are incorporated herein by reference.

More specifically the following synthetic schemes are useful in preparing the cephalosporin sulfone esters or amides of formula (I).

(1) As exemplified by Example 16

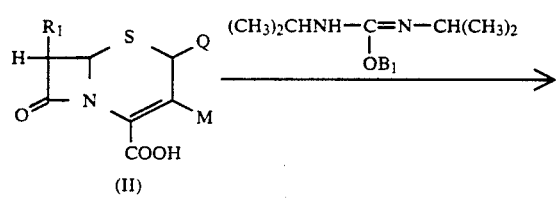

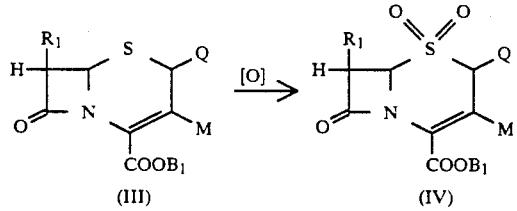

wherein $B_1$ represents $C_{1-6}$alkyl such as methyl, ethyl, i- or n-propyl or t-butyl or aralkyl such as m-methoxycarbonylbenzyl or other substituted or unsubstituted alkyl groups.

(2) As exemplified by Example 18

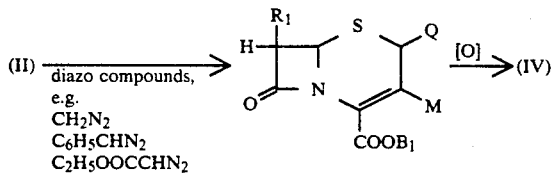

(3) Acidic addition method

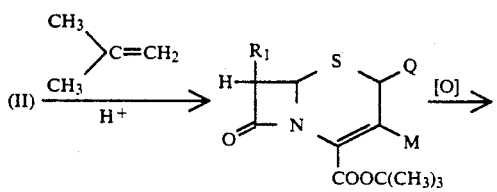

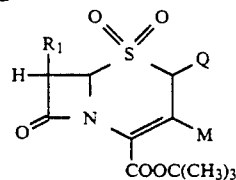

(4) Displacement method as illustrated in Example 19

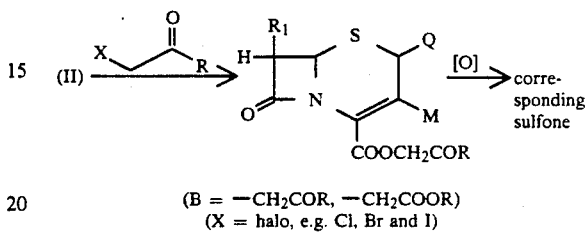

(B = $-CH_2COR$, $-CH_2COOR$)
(X = halo, e.g. Cl, Br and I)

(5) Aminolysis of an anhydride as exemplified in Example 20

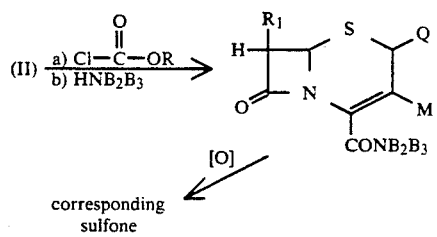

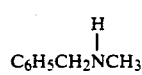

wherein R is loweralkyl, e.g. isobutyl, $HNB_2B_3$ is $$C_6H_5CH_2\overset{H}{\underset{|}{N}}CH_3$$

or other substituted or nonsubstituted amine.

(6) DCC coupling method as exemplified in Example 21 and Examples 32-33

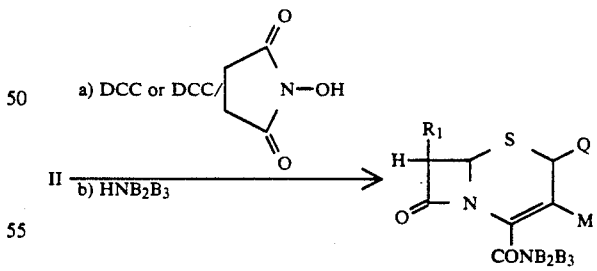

wherein DCC represents dicyclohexylcarbodiimide $HNB_2B_3$ is $H_2NCH_2COOR$ (wherein R is $C_{1-6}$alkyl or aralkyl) or other substituted or unsubstituted amine.

It should be noted that when it is appropriate, (II) can be oxidized first to a sulfone and then subject to esterification or amidation according to schemes (1) to (6). Furthermore, (II) can also be a 7,7-disubstituted compound, e.g., 7-halo-7-R-derivative.

The starting compound of formula (II) and methods for the preparation thereof are known in most cases as they are well-known antibiotics and have been explored extensively The following schemes, however, illustrate the preparation of a few representative precursors:

(A) Modifications at 7-position—Diazotization reactions (1) As exemplified by Examples 1, 7 and 8

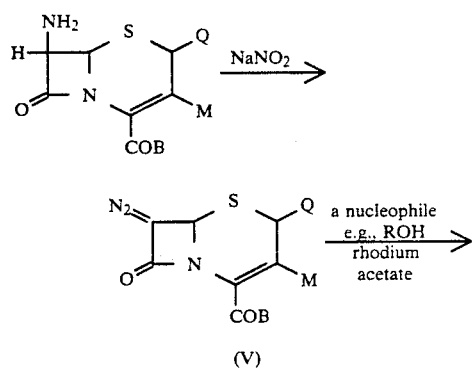

wherein R is as defined above.

(2) As exemplified by Examples 2, 3, 6, 7 and 23

(a)

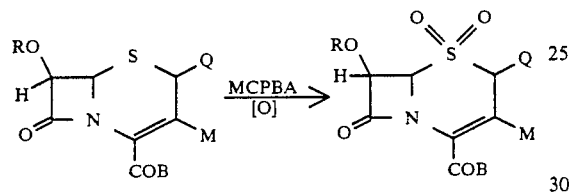

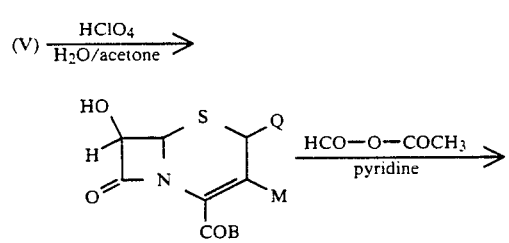

(b)

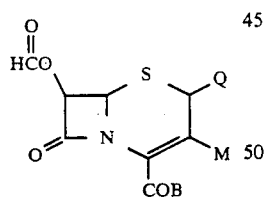

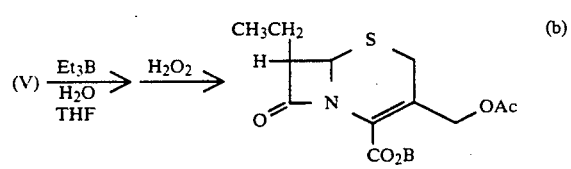

(c)

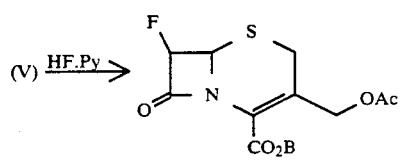

In (a) to (c), B is t-butyl or other group as previously defined.

(B) Modification at 3-position (1) As exemplified in Example 4, Steps C–E

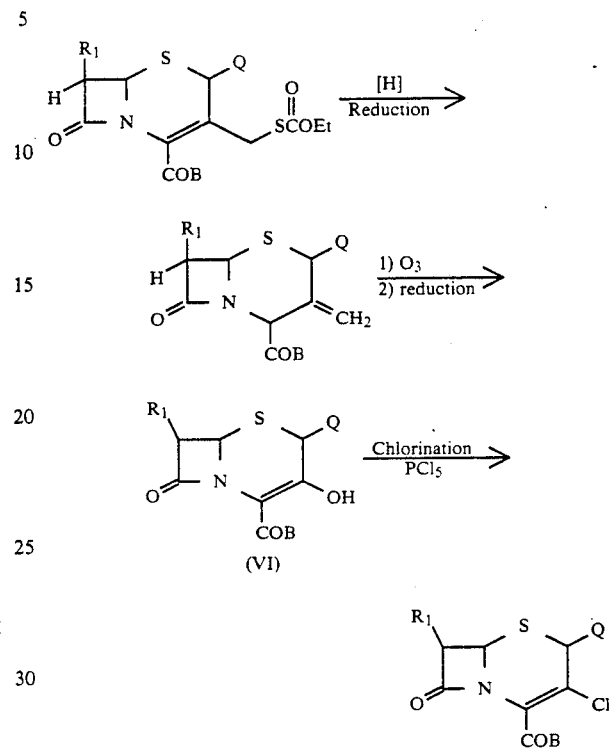

(2) As exemplified in Example 5 ($R_1$=OCH$_3$)

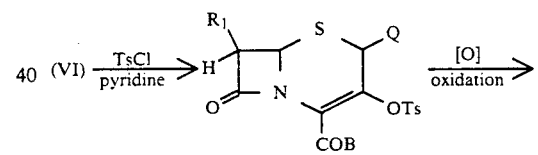

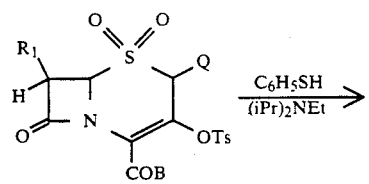

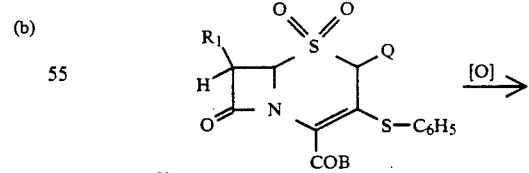

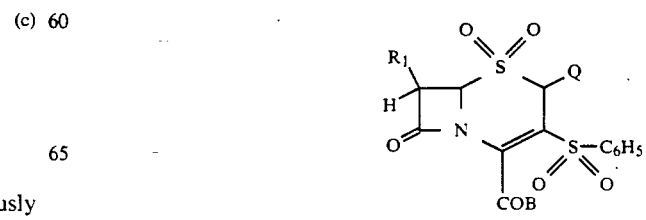

(3) As exemplified in Examples 8–10 and 12–14
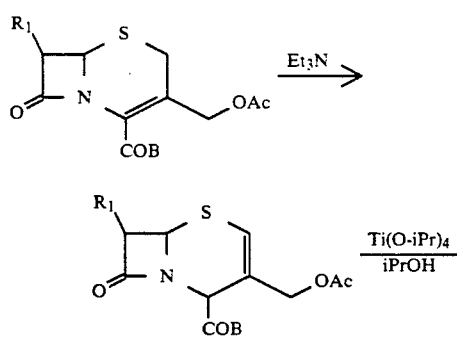
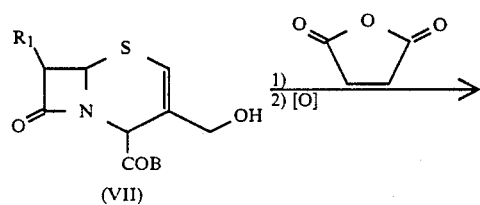
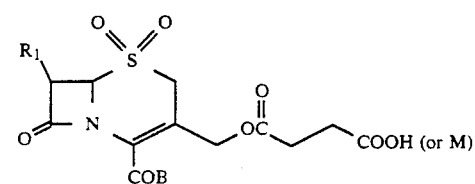
(4) As exemplified in Example 11
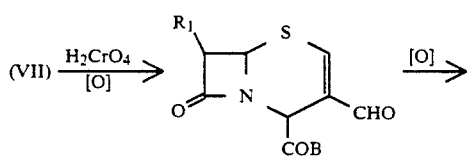
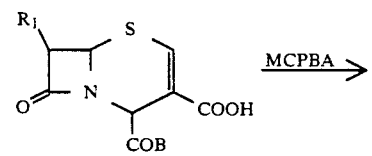
(5) As exemplified in Example 15
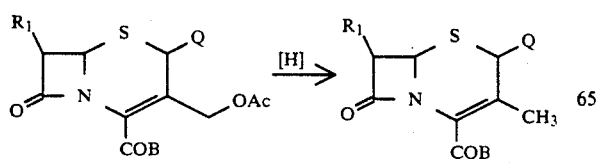
(6) As exemplified in Examples 28–31
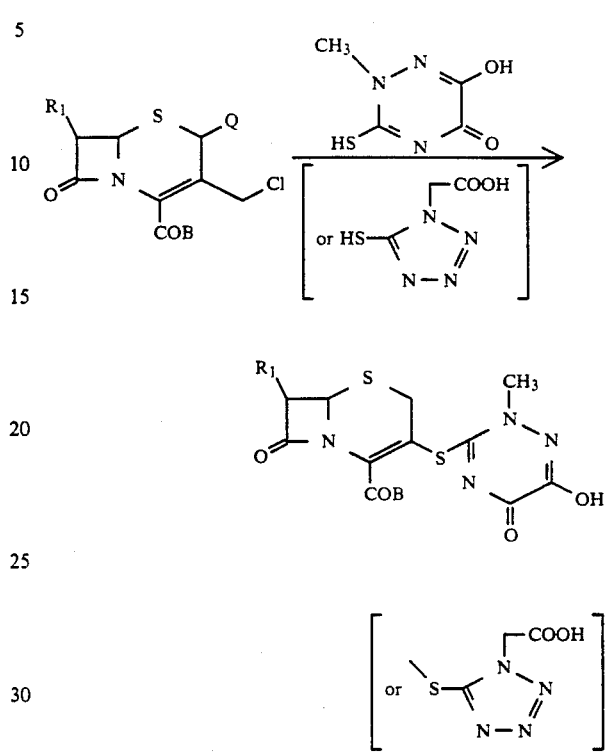
(C) Modification of the 4-position (introduction of substituent O) as exemplified in Examples 24–28
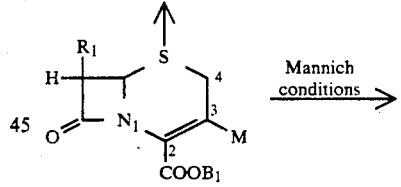
(1)
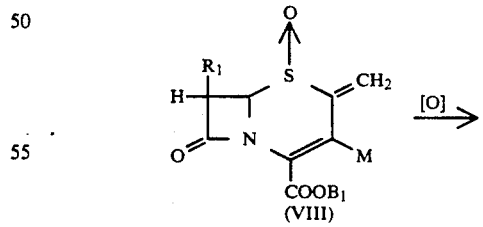
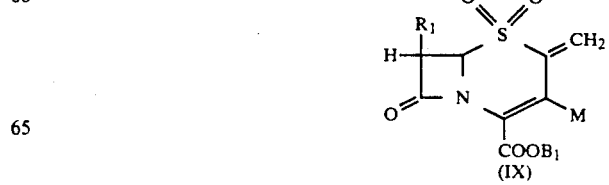

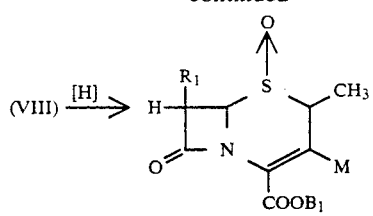
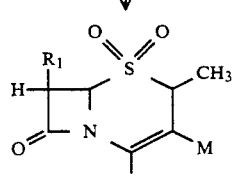
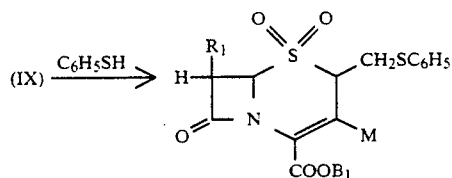
(D) Specific Synthesis of 3-acetyloxymethyl-7α-methoxy-8-oxo-5-thia-1-azabicyclo[4.2.0]oct-2-ene-2-(2-(S)-carboxypyrrolidinecarboxamide)-5,5-dioxide (Compound A)
This compound is prepared according to the following scheme. The detailed synthesis is described in Example 34.
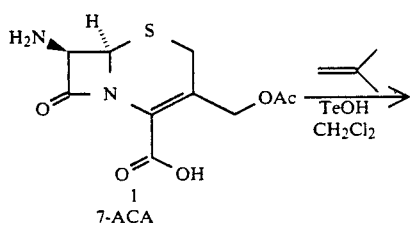
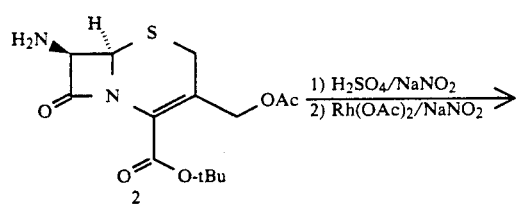
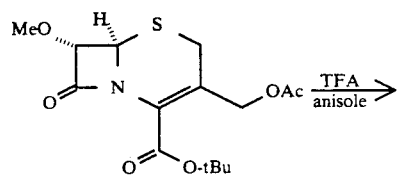
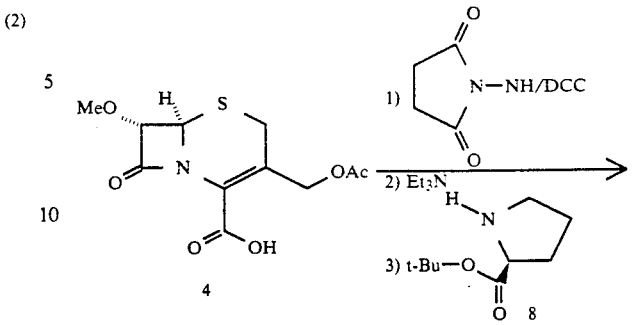
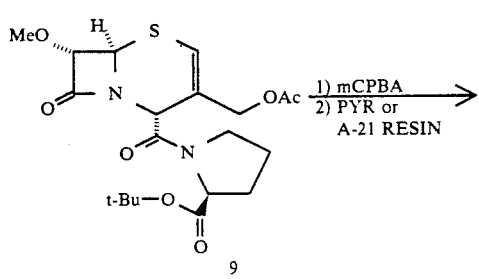
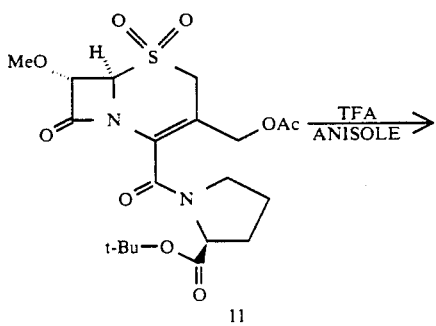
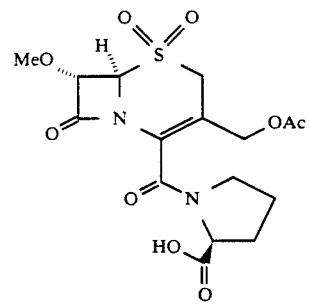
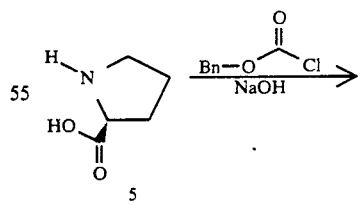
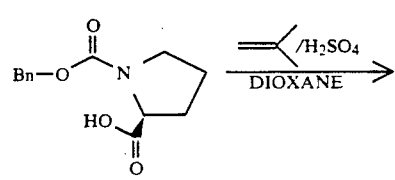

-continued

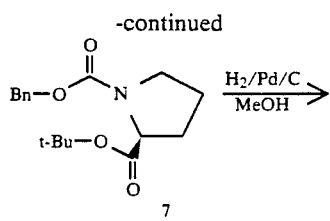

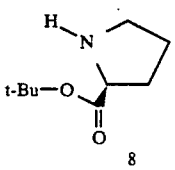

This invention also relates to a method of treating inflammation in patients using a compound of Formula (I), particularly an especially preferred compound as the active constituent It has been found that the compounds of Formula (I) have anti-inflammatory antidegeneration activity and are effective in the prevention and inhibition of edema and granuloma tissue formation as shown below in Table II by the effective inhibition of the proteolytic function of human granulocyte elastase.

TABLE II

| $R_1$ | M | B | Q | $ED_{50}$ |
|---|---|---|---|---|
| —$OCH_3$ | —$CH_2OCOCH_3$ | —$OCH_3$ | H | 0.08 |
| " | " | —$OCH_2\phi$ | H | 0.03 |
| " | " | —$OCH_2\phi$-(p-$COOCH_3$) | H | 0.02 |
| " | " | —$OCH_2COtBu$ | H | 0.02 |
| " | " | —$OCH_2CH=C(CH_3)_2$ | H | 1.0 |
| " | " | —$O(CH_2)_3COOCH_3$ | H | 0.05 |
| " | " | —$NHCH_2COOtBu$ | H | 0.9 |
| " | " | —$N(CH_3)_2$ | H | 0.6 |
| " | " | —OtBu | $CH_3$ | 0.03 |
| " | " | —OtBu | $CH_2$ | 0.03 |
| —$OCH_3$ | —$CH_2OCOCH_3$ | —OtBu | $CH_2S\phi$ | 0.03 |
| " | " | —OtBu | $CH_2SO_2\phi$ | 0.02 |
| " | " | —OtBu | $CH_2\phi$ | 15.0 |
| —$C_2H_5$ | " | OtBu | H | 1.0 |
| " | —$CH_2OCONHCHCOOH$<br>                    $\|$<br>                      $CH_3$ | OtBu | H | 1.0 |
| " | —$CH_2OCOCH_2CH_2COOH$ | OtBu | H | 0.8 |
| " | —$CH_2OCOCH_3$ | —$OCH_2\phi$ | H | 0.4 |
| " | —$CH_2OCOCH\phi$<br>         $\|$<br>         $NH_2$ | —OtBu | H | 0.4 |
| —$OCH_3$ | —$CH_2OCOCH_3$ | (N-methylpyrrolidine ester) | H | 5 |
| " | " | —$N(CH_3)CH_2COOH$ | H | |
| " | " | (triazine ring structure) | " | H |

TABLE II-continued

| $R_1$ | M | B | Q | $ED_{50}$ |
|---|---|---|---|---|
| " | " | ![N-methylpyrrolidine-2-carboxylate] | H | |
| OCH₃ | CH₂OCOCH₃ | —NH(CH₂)₃COOtBu | H | 0.1 |
| " | " | —N(CH₃)CH₂φ | H | 0.06 |
| " | " | —OtBu | H | 0.5 |
| —OC₆H₅ | " | " | H | 0.8 |
| —F | " | " | H | 0.03 |
| —Cl | " | " | H | 0.02 |
| —OCHO | " | " | H | 0.15 |
| —OCHO | " | —OCH₃ | H | 0.1 |
| —OCOCH₃ | " | —OCH₂φ | H | 0.4 |
| —OCH₃ | —CH₂OH | —OtBu | H | 0.8 |
| " | —CH₂OCOCH₂CH₂—COOH | " | H | 0.1 |
| " | —CH₂OCOCH₂NHCH₃ | " | H | 0.3 |
| OCH₃ | —CH₂OCO-φ-(O—COOH) | —OtBu | H | 0.6 |
| " | —CH₂OCOCH₂N(CH₃)COOtBu | " | H | 0.1 |
| " | —CH₂OCOOC₂H₅ | " | H | 0.3 |
| " | —CH₂Cl | " | H | 0.15 |
| " | —CH₂S-(5-triazolyl) | " | H | 0.9 |
| " | —CH₂—SC(=S)OC₂H₅ | " | H | 0.7 |
| —OCH₃ | —CH₂S-(N-methylimidazolyl) | —OtBu | H | 1.0 |
| " | —CH₂OCH₃ | " | H | 0.3 |
| " | —CH₂S-(5-methyl-1,3,4-thiadiazolyl) | " | H | 1.0 |
| —OCH₃ | —CH₂S-(benzothiazolyl) | —OtBu | H | 3.0 |

TABLE II-continued

[Structure: β-lactam with sulfone, R1, H at one carbon, N, C=O, with M substituent and COB group, Q position]

| R1 | M | B | O | ED50 |
|---|---|---|---|---|
| " | [pyrazole: -CH2S-C(=N-NH-N=)] | " | H | 0.6 |
| " | [triazole with CH3: -CH2S-C with N-CH3, N=N, N ring] | " | H | 0.6 |
| " | —CH2OCONHCH2COOH | " | H | 0.04 |
| " | —COOH | " | H | 0.01 |
| " | —CH2Sφ | " | H | 0.4 |
| " | —CH2SOφ | " | H | 0.08 |
| " | —CH2SO2φ | " | H | 0.2 |
| —OCH3 | —Cl | —OCH3 | H | 0.2 |
| " | —CH2SO2CH3 | —OtBu | H | 0.1 |
| —OCH3 | —CH3 | —OtBu | H | 1.0 |
| " | —CH3 | —OCH2COOC2H5 | H | 0.5 |
| " | —CH3 | —OCH2φ-(mCOOCH3) | H | 0.3 |

φ = C6H5— or C6H4 i.e., phenyl

TABLE IIa

| Compound | ED50 |
|---|---|
| [Structure: β-lactam sulfone with Cl, Cl substituents, CH2-OAc, COOt-Bu] | 0.1 |
| [Structure: β-lactam sulfone with F, F substituents, CH2-OAc, COOt-Bu] | 0.05 |

TABLE III

Protocol—Enzyme Assays for the Inhibition of Human Polymorphonuclear Leukocyte Elastase Via Hydrolysis of N-t-Boc-alanyl-alanyl-prolylalanine-o-nitroanilide Reagents:

0.05M TES (N-tris[hydroxymethyl]methyl-2-aminoethanesulfonic acid) Buffer, pH 7.5.

0.2 mM N-t-Boc-alanyl-alanyl-prolyl-alanine-p-nitroanilide (Boc-AAPAN).

To prepare substrate, the solid (m.w. 550) was first dissolved in 10.0 ml DMSO. Buffer at pH 7.5 was then added to a final volume of 100 ml.

Crude extract of human polymorphonuclear leukocytes (PMN) containing elastase activity.

Inhibitors (cephalosporin sulfone esters) to be tested dissolved in DMSO just before use.

Assay Procedure:

To 1 0 ml of 0 2 mM Boc-AAPAN in a cuvette, 0.01–0.1 ml of DMSO with or without inhibitor was added. After mixing, a measurement was taken at 410 mμ to detect any spontaneous hydrolysis due to presence of test compound. 0.05 Milliliters of PMN extract was then added and the ΔOD/min at 410 mμ was measured and recorded. Beckman model 35 spectrophotometer was used.

Results:

Results were reported as ED50, i.e., effective dosage in micrograms per milliliter (μg/ml) for 50% inhibition of the enzyme activity 2 minutes after zero time.

Comments:

The elastase activity in the crude PMN extract may vary from one preparation to another. A control of each new batch is run, and the volume added in the assay procedure is adjusted according to activity.

Accordingly, the compounds of Formula (I) can be used to reduce inflammation and relieve pain in diseases such as emphysema, rheumatoid arthritis, osteoarthritis, gout, bronchial inflammation, infectious arthritis, rheumatic fever and the like.

For treatment of inflammation, fever or pain, the compounds of Formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, maize starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate or condensation products of ethylene oxide with partial esters derived from fatty acids and hexitol anhydrides, for example polyoxyethylene sorbitan monooleate. The said aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally occurring gums, for example gum acacia or gum tragacanth, naturally-occurring phosphatides, for example soy bean, lecithin, and esters or partial esters derived from fatty acids and hexitol anhydrides, for example sorbitan mono-oleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of Formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the anti-inflammatory agents are employed.

Dosage levels of the order to 0.2 mg to 140 mg per kilogram of body weight per day are useful in the treatment of the above-indicated conditions (10 mg to 7 gms. per patient per day). For example, inflammation is effectively treated and anti-pyretic and analgesic activity manifested by the administration from about 0.5 to 50 mg of the compound per kilogram of body weight per day (25 mg to 3.5 gms per patient per day). Advantageously, from about 2 mg to about 20 mg per kilogram of body weight per daily dosage produces highly effective results (50 mg to 1 gm per patient per day).

The amount of active ingredient that may be combined with the carrier materials to produce a single dosage form will vary depending upon the host treated and the particular mode of administration. For example, a formulation intended for the oral administration of humans may contain from 5 mg to 5 gm of active agent compounded with an appropriate and convenient amount of carrier material which may vary from about 5 to about 95 percent of the total composition. Dosage unit forms will generally contain between from about 25 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

EXAMPLE 1 t-Butyl-3-acetyloxymethyl-7α-methoxy-8-oxo-5-thia-1-azabicyclo[4.2.0]oct-2-ene-2-carboxylate-5,5-dioxide

Step A: Preparation of t-Butyl 3-acetyloxymethyl-7-diazo-8-oxo-5-thia-1-azabicyclo[4.2.0]oct-2-ene-2-carboxylate Into a two-liter Erlenmeyer flask is placed a solution of 7-ACA tert-butyl ester (7-ACA=3-acetyloxymethyl-7β-amino-8-oxo-5-thia-1-azabicyclo[4.2.0]oct-2-ene-2-carboxylate (22.22 g; 0.067 mol;) in $CH_2Cl_2$ (500 ml). To this solution was added a mixture of sodium nitrite (4.68 g, 0.067 mol) in water (500 ml). The resulting two-phase mixture was cooled in an ice bath, and then 2N aqueous $H_2SO_4$ (51 ml) was added dropwise over 30 minutes with vigorous stirring. Stirring was continued for one hour at 0°, then the layers were separated and the aqueous layer was washed with methylene chloride (200 ml). The organic layers were combined, washed with brine (250 ml), dried over $MgSO_4$, and filtered to give a yellow solution of the diazo product which is used directly in the next reaction.

Step B: Preparation of t-Butyl 3-acetyloxymethyl-7α-methoxy-8-oxo-5-thia-1-azabicyclo[4.2.0]oct-2-ene-2-carboxylate The solution of t-butyl 3-acetyloxymethyl-7-diazo-8-oxo-5-thia-1-azabicyclo[4.2.0]oct-2-ene-2-carboxylate was cooled in an ice bath, and methanol (525 ml) was added. To this chilled mixture was added Rhodium (II) acetate dimer (210 mg), and the reaction mixture was stirred for 45 minutes, during which time the color changes from yellow to green-brown. The reaction mixture was filtered through silica gel, concentrated and dried in vacuo to give a dark red oil which was then purified by preparative high-pressure liquid chromatography to give 9.62 g (41.4%) of t-butyl 3-acetyloxymethyl-7α-methoxy-8-oxo-5-thia-1-azabicyclo[4.2.0]oct-2-ene-2-carboxylate as a yellow oil.

Step C: Preparation of t-Butyl-3-acetyloxymethyl-7α-methoxy-8-oxo-5-thia-1-azabicyclo[4.2.0]oct-2-ene-2-carboxylate 5dioxide In a 50 ml round bottom flask were placed t-butyl 3-acetyloxymethyl-7α-methoxy-8-oxo-5-thia-1-azabicyclo[4.2.0]oct-2-ene-2-carboxylate (2.07 g, 6.03 mmoles) and $CH_2Cl_2$ (25 ml). The resulting mixture was stirred under nitrogen with ice bath cooling, then meta-chloroperbenzoic acid (2.0 g, 80–90% pure) was added, the ice bath was removed, and stirring was continued for two hours. The reaction mixture was diluted with ethyl acetate (50 ml), filtered and then washed with saturated sodium bicarbonate (100 ml), water (100 ml) and then saturated brine (50 ml). The organic layer was dried over $MgSO_4$, and concentrated to give 2.20 g crude product. This product was purified by preparative HPLC using hexane:ethyl acetate (2:1) to give a white solid further purified by recrystallization from EtOAc/Hex to give 1.23 g (54.3%) of analytically pure t-butyl-3-acetyloxymethyl-7α-methoxy-B-oxo-5-thia-1-azabicyclo[4.2.0]oct-2-ene-2-carboxylate 5,5-dioxide m.p. 127°.

Calcd. for $C_{15}H_{21}NO_8S$

|  | C (%) | H | N | S |
|---|---|---|---|---|
|  | 47.99 | 5.64 | 3.73 | 8.54 |
| Found: | 48.05 | 5.68 | 3.57 | 8.53 |

Following the same procedure described above but substituting for the 7-ACA tert-butyl ester used therein, t-butyl 3-methyl-7β-amino-8-oxo-5-thia-1-azabicyclo[4.2.0]oct-2-ene-2-carboxylate, there was prepared 152 mq (24% yield) of t-butyl 3-methyl-7α-methoxy-B-oxo-5-thia-1-azabicyclo[4.2.0]oct-2-ene-2-carboxylate.

EXAMPLE 2 t-Butyl-3-acetyloxymethyl-7α-formyloxy-8-oxo-5-thia-1-axabicyclo[4.2.0]oct-2-ene-2carboxylate-5,5-dioxide

Step A: Preparation of t-Butyl 3-acetyloxymethyl-7α-hydroxy-8-oxo-5-thia-1-azabicyclo[4.2.0]oct-2-ene-2-Carboxylate Crude t-butyl 3-acetyloxymethyl-7-diazo-8-oxo-5-thia-1-azabicyclo[4.2.0]oct-2-ene-2-carboxylate (prepared from 20.5 %, i.e. 63 mmole of t-butyl ester of 7-ACA) was taken up in 400 ml of acetone and 400 ml of water containing 80 ml of 1N perchloric acid was added at room temperature. The reaction was stirred for 3 hours (or until nitrogen evolution ceases) and was then diluted with water and extracted twice with methylene chloride. The organic phases were washed with saturated aqueous sodium bicarbonate solution and saturated aqueous sodium chloride solution, dried over sodium sulfate and evaporated in vacuo. The residue was chromatographed on silica gel with 30% ethyl acetate-hexane to give 2.75 g (13%) of t-butyl 3-acetyloxymethyl-7α-hydroxy-8-oxo-5-thia-1-azabicyclo[4.2.0]oct-2-ene-2-carboxylate as a white solid, NMR ($CDCl_3$) δ 1.53 (s, 9), 2.07 (s, 3), 3.35 (ABq, 2, 18 Hz), 4.5–5.0 (m, 4).

Step B: Preparation of t-Butyl 3-acetyloxymethyl-7α-formyloxy-8-oxo-5-thia-1-azabicyclo[4.2.0]oct-2-ene-carboxylate To a solution of 1.5 g (4.6 mmols) of t-butyl 3-acetyloxymethyl-7α-hydroxy-B-oxo-5-thia-1-azabicyclo4.2.0]oct-2-ene-2-carboxylate in 50 ml of methylene chloride at 0° C. was added 1.5 ml of acetic-formic anhydride reagent (prepared by cooling 2 volumes of acetic anhydride to 0° C., slowly adding 1 volume of 96% formic acid, heating at 50° for 15 minutes and cooling) followed by 1.2 ml of pyridine. The reaction was allowed to warm to room temperature, stirred for 2 hours and then quenched by addition of ice water. The layers were separated and the organic layer was washed with saturated aqueous sodium bicarbonate solution and saturated aqueous sodium chloride solution, dried over sodium sulfate and evaporated in vacuo. The residue was triturated with 30% ethyl acetate-hexane to give 700 mg (43%) of t-butyl-3-acetyloxymethyl-7α-formyloxy-8-oxo-5-thia-1-azabicyclo[4.2.0]oct-2-ene-2-carboxylate, NMR (CDCl₃) δ 1.53 (s, 9), 2.03 (s, 3), 3.40 (AB q, 2, 17 Hz), 4.67 (d, 1, 2 Hz) 4.78 (ABq, 2, 13 Hz), 5.49 (br d, 1, 2 Hz), 7.99 (s, 1).

Step C: Preparation of t-Butyl-3-acetyloxymethyl-7α-formyloxy-8-oxo-5-thia-1-azabicyclo[4.2 0]oct-2-ene-2-carboxylate-5,5-dioxide Following substantially the same procedure as described in Example 1, Step C, 750 mg of t-butyl 3-acetyloxymethyl-7α-formyloxy-8-oxo-5-thia-1-azabicyclo[4.2.0]oct-2-ene-2-carboxylate was oxidized to 545 mg (67%) of t-butyl-3-acetyloxymethyl-7α-formyloxy-8-oxo-5-thia-1-azabicyclo[4.2.0]oct-2-ene-2-carboxylate-5,5-dioxide as a white solid, m.p. 171°–172° C. dec.

EXAMPLE 3 t-Butyl-3-acetyloxymethyl-7α-acetyloxy-8-oxo-5-thia-1-azabicyclo[4.2.0]oct-2-ene-2-carboxylate-5.5-d(oxide

Step A: Preparation of t-butyl 3-acetyloxymethyl-7α-acetyloxy-8-oxo-5-thia-1-azabicyclo[4.2.0]oct-2-ene-2-carboxylate To a solution of 240 mg (0.73 mmoles) of t-butyl-3-acetyloxymethyl-7α-hydroxy-B-oxo-5-thia-1-azabicyclo[4.2.0]oct-2-ene-2-carboxylate in 10 ml of methylene chloride at 0° C. was added 85 mg (1.1 mmols) of acetyl chloride and 90 mg (1.1 mmols) of pyridine. The ice bath was removed and the reaction was stirred at room temperature for 3 hours The reaction was then poured into ice water and the layers separated. The organic layer was washed with saturated aqueous sodium bicarbonate solution and saturated aqueous sodium chloride, dried over sodium sulfate, and evaporated. Chromatography on silica gel with 30% ethyl acetate-hexane and trituration with hexane gave 100 mg (37%) of t-butyl-3-acetyloxymethyl-7α-acetyloxy-8-oxo-5-thia-1-azabicyclo[4 2.0]oct-2-ene-2-carboxylate as a white solid, m.p. 94°–95° C. with decomposition.

Step B: Preparation of t-Butyl-3-acetyloxymethyl-7α-acetyloxy-8-oxo-5-thia-1-azabicyclo [4.2.0]oct-2-ene-2-carboxylate-5,5-dioxide Following the same procedure as described in Step C, Example 1, 100 mg of t-butyl-3-acetyloxymethyl-7α-acetyloxy-8-oxo-5-thia-1-azabicyclo[4.2.0]-oct-2-ene-2-carboxylate was oxidized to t-butyl-3-acetyloxymethyl-7α-acetyloxy-8-oxo-5-thia-1-azabicyclo[4.2.0]oct-2-ene-2-carboxylate-5,5-dioxide m.p. 126°–129° C.

EXAMPLE 4

Methyl-3-chloro-7α-methoxy-8-oxo-5-thia-1-azabicyclo[4.2.0]oct-2-ene-2-carboxylate-5,5-dioxide

Step A: Preparation of Methyl 3-ethoxycarbonylthiamethyl-7β-amino-8-oxo-5-thia-1-azabicyclo [4.2.0]oct-2-ene-2-carboxylate To a vigorously stirred suspension of 8 g (23.9 mmols) of 3-ethoxycarbonyl-thiamethyl-7β-amino-8-oxo-5-thia-1-azabicyclo[4.2.0]oct-2-ene-2-carboxylic acid in 300 ml of methanol was slowly added a solution of diazomethane in ethyl ether until most of the solid dissolves The excess diazomethane was quenched after 5 minutes by addition of acetic acid. The reaction was then poured into ice water and extracted twice with ethyl acetatemethyl ether (1:1). The organic layers were washed with water and saturated aqueous sodium chloride solution, dried over sodium sulfate and evaporated in vacuo.

The residue was flash chromatographed eluting with a solvent gradient of 50 to 70% ethyl acetate-hexane to give 4.5 g (54%) of methyl 3-ethoxycarbonylthiamethyl-7β-amino-8-oxo-5-thia-1-azabicyclo[4.2.0]oct-2-ene-2-carboxylate as a white solid, NMR (CDCl₃) δ 1.40 (t, 3, 7 Hz), 1.73 (br s, 1) 3.53 (ABq, Z, 19 Hz), 3.87 (s, 3), 4.30 (ABq, 2, 13 Hz), 4.5–5.0 (m, 4).

Step B: Preparation of Methyl 3-ethoxycarbonylthiamethyl-7ζ-methoxy-8-oxo-5-thia-1-azabicyuclo[4.2.0]oct-2-ene-2-carboxylate Following substantially the same procedures as described in Example 1, Steps A and B, 4.5 g (12.9 mmoles) of methyl 3-ethoxycarbonylthiamethyl-7β-amino-8-oxo-5-thia-1-azabicyclo[4.2.0]oct-2-ene-2-carboxylate carboxylate were converted to 1.2 g (26%) of methyl 3-ethoxycarbonylthiamethyl-7α-methoxy-8-oxo-5-thia-1-azabicyclo[4.2.0]oct-2-ene-2-carboxylate as a yellowish solid, NMR (CDCl₃) δ 1.38 (t, 3, 7 Hz), 3.43 (ABq, 2, 18 Hz), 3.51 (s, 3), 3.86 (s, 3H), 4.22 (HBq, 2, 13 Hz), 4.3–4.7 (m, 4).

Step C: Preparation of Methyl 3-methylene-7α-methoxy 8-oxo-5-thia-1-azabicyclo[4.2.0]oct-2-ene-2-carboxylate To a suspension of 8 g of Raney nickel in 70 ml of water under nitrogen was added 1.2 g (3.3 mmoles) of methyl 3-ethoxycarbonylthiamethyl-7α-methoxy-8-oxo-5-thia-1-azabicyclo[4.2.0]oct-2-ene-2-carboxylate in 70 ml of ethanol.

The mixture was hydrogenated at 40 psi of hydrogen in a Parr shaker at room temperature for 16 hours. The catalyst was then removed by filtration and the filtrate was diluted with water and extracted twice with ethyl acetate. The organic layers were washed with water and saturated aqueous sodium chloride solution, dried over sodium sulfate and evaporated in vacuo. The residue was flash chromatographed eluting with a solvent gradient of 30 to 40% ethyl acetate-hexane to give 500 mg (62%) of methyl 3-methylene-7α-methoxy-8-oxo-5-thia-1-azabicyclo[4.2.0]oct-2-ene-2-carboxylate as a colorless oil, NMR (CDCl₃) δ 3.33 (ABq, 2, 14 Hz), 3.56 (s, 3), 3.73 (s, 3), 4.40 (br s, 1), 5.0–5.3 (m, 4).

Step D: Preparation of Methyl 3-hydroxy-7α-methoxy-8-oxo-5-thia-1-azabicyclo[4.2.0]oct-2-ene-2-carboxylate A solution of 200 mg (0.82 mmols) of methyl 3-methylene-7α-methoxy-8-oxo-5-thia-1-azabicyclo[4.2.0]oct-2-ene-2-carboxylate in 15 ml of methylene chloride was cooled to -70° C. in a dry ice-acetone bath. Ozone was bubbled through the solution until the first sign of blue coloration was noticed. Nitrogen was then bubbled through to flush out the excess ozone, 2 g of sodium bisulfite were added and the suspension was vigorously stirred at 0° C. for 30 minutes.

The reaction was filtered and the filtrate was evaporated in vacuo to give crude product which was used directly in the next step.

Step E: Preparation of Methyl 3-chloro-7α-methoxy-8-oxo-5-thia-1-azabicyclo[4.2.0]oct-2-ene-2-carboxylate The crude methyl 3-hydroxy-7α-methoxy-8-oxo-5-thia-1-azabicyclo[4.2.0]oct-2-ene-2-carboxylate (approximately 0.82 mmols) was taken up in 10 ml of dimethylformamide and slowly added to a solution of 680 mg (3.3 mmols) of phosphorous pentachloride in 10 ml of dimethylformamide at −60° C. (prepared by stirring at −10° C. for 15 minutes, then cooling to −60° C.). The solution was stirred at −60° C. for 30 minutes, then at −10° C. for 90 minutes before it was quenched by pouring into water/ethyl acetate. The organic layer was washed with saturated aqueous sodium bicarbonate solution and saturated aqueous sodium chloride solution, dried over sodium sulfate and evaporated in vacuo to give a crude residue of methyl 3-chloro-7α-methoxy-8-oxo-5-thia-1-azabicyclo[ 4.2.0]oct-2-ene-2-carboxylate This was oxidized directly to afford 4.9 mg of methyl 3-chloro-7α-methoxy-8-oxo-5-thia-1-azabicyclo[4.2.0]oct-2-ene-2-carboxylate-5,5-dioxide (according to procedures described in Example 1, Step C.) NMR (CDCl₃) δ 3.57 (s, 3), 3.90 (s, 3), 4.00 (ABq, 2, 18 Hz), 4.67 (brS, 1), 5.10 (d, 1, 2 Hz).

EXAMPLE 5

Methyl 3-phenylthio (or 3-phenylsulfonyl)-7α-methoxy-8-oxo-5-thia-1-azabicyclo[4.2.0]oct-2-ene-2-carboxylate-5,5-dioxide Step A: Preparation of Methyl 3-tosyloxy-7α-methoxy-8-oxo-5-thia-1-azabicyclo[4.2.0]oct-2-ene-2-carboxylate-5,5-dioxide A solution of 450 mg of crude methyl 3-hydroxy-7α-methoxy-8-oxo-5-thia-1-azabicyclo[4.2.0]oct-2-ene-2-carboxylate in 5 ml of pyridine was stirred with 470 mg (2.4 mmols) of tosyl chloride at 0° C. for 3 hours. The reaction mixture was poured into ice water and extracted twice with ethyl acetate. The organic layers were washed twice with dilute aqueous hydrochloric acid and saturated aqueous sodium chloride, dried over sodium sulfate and evaporated in vacuo to give a crude residue of methyl 3-tosyloxy-7α-methoxy-8-oxo-5-thio-1-aza-bicyclo[4.2.0]oct-2-ene-2-carboxylate. This is directly oxidized in accordance with the same procedure of Example 1, Step C to give 180 mg (20%) of methyl 3-tosyloxy-7α-methoxy-8-oxo-5-thia-1-azabicyclo[4.2.0]oct-2-ene-2-carboxylate-5,5-dioxide as a white solid, NMR (CDCl₃) δ 2.47 (s, 3), 3.57 (s, 3), 3.70 (s, 3), 4.10 (ABq, 2, 18 Hz), 4.67 (m, 1), 5.07 (d, 1, 2 Hz), 7.50 (ABq, 4, 9 Hz).

Step B: Preparation of Methyl 3-phenylthio-7α-methoxy-8-oxo-5-thia-1-azabicyclo[4.2.0]oct -2-ene-2-carboxylate-5,5-dioxide A solution of 170 mg (0.40 mmols) of methyl 3-tosyloxy-7α-methoxy-B-oxo-5-thia-1-azabicyclo[4.2.0]oct-2-ene-2-carboxylate-5,5-dioxide in 2 ml of N,N-dimethylformamide was stirred with 50 μl (0.40 mmols), of thiophenol and 50 μl (0.40 mmols) of N-ethyl-N,N-diisopropylamine at −10° C. for 30 minutes. The reaction was poured into ice water and extracted twice with ethyl acetate. The organic layers were washed with dilute hydrochloric acid and saturated aqueous sodium chloride solution, dried over sodium sulfate and evaporated. The residue was chromatographed on 2×2000 μm silica preparative plates using 40% ethyl acetate-hexane. Since the product band still contained some of the higher R_f impurity (the major product), it was rechromatographed on a 1000 μm silica preparative plate to give 15 mg (10%) of methyl 3-phenylthio-7α-methoxy-8-oxo-5-thia-1-azabicyclo[4.2.0]oct-2-ene-2-carboxylate-5,5-dioxide, NMR (CDCl₃) δ 3.53 (s, 3), 3.57 (ABq, 2, 18 Hz), 3.87 (s, 3), 4.51 (br s, 1), 5.00 (d, 1, 2 Hz), 7.33 (br s, 5).

Step C: Preparation of Methyl 3-phenylsulfonyl-7α-methoxy-8-oxo-5-thia-1-azabicyclo[4.2.0]oct-2-ene-2-carboxylate-5,5-dioxide A solution of 11 mg (0.030 mmole) methyl 3-phenylthio-7α-methoxy-8-oxo-5-thia-1-azabicyclo[4.2.0]oct-2-ene-2-carboxylate-5,5-dioxide in 1 ml of methylene chloride was stirred with 12 mg (0.060 mmols) of m-chloroperbenzoic acid at 0° C. for 30 minutes. The entire reaction was then chromatographed on a 1000 μm silica preparative plate eluting with 50% ethyl acetate-hexane to give 8 mg (67%) of methyl 3-phenylsulfonyl-7α-methoxy-8-oxo-5-thia-1-azabicyclo-[4.2.0]oct-2-ene-2-carboxylate-5,5-dioxide. NMR (CDCl₃) δ 3.36 (d, 1, 18 Hz), 3.53 (s, 3), 3.96 (s, 3), 4.20 (br d, 1, 18 Hz), 4.70 (br s, 1), 5.06 (d, 1, 2 Hz), 7.2–7.8 (m, 5).

EXAMPLE 6 t-Butyl 3-acetyloxymethyl-7α-fluoro-8-oxo-5-thia-1-azabicyclo[4.2.0]oct-2-ene-2-carboxylate-5,5-dioxide Step A: Preparation of t-Butyl 3-acetyloxymethyl-7α-fluoro-8-oxo-5-thia-1-azabicyclo[4.2.0]oct-2-ene-2-carboxylate t-Butyl 3-acetyloxymethyl-7-diazo-8-oxo-5-thia-1-azabicyclo[4.2.0]oct-2-®ne-2-carboxylate was prepared from 10 mmoles 7-amino derivatives in the same manner as described in Step A, Example 1, and taken up in 25 ml dry methylene chloride. To it with stirring was added dropwise over 30 seconds 0.60 ml 70% HF in pyridine. The mixture was stirred 2 5 minutes more and then washed with aq K₂HPO₄, water, aq H₃PO₄ and brine. It was dried with MgSO₄, filtered and chromatographed on 164 silica gel with 1:1 hexane-ethyl acetate, affording 183 mg of t-butyl 3-acetyloxymethyl-7≡-fluoro-8-oxo-5-thia-1-azabicyclo[4.2.0]oct-2-ene-2-carboxylate. IR(μ): 5.57, 5.76. NMR (CDCl₃): δ 1.54 s, t-Bu; 2.08 s, Ac; 3.34 d of d, J = 18, 1.9 Hz, and 3.58 d of d, J = 18, 0.8 Hz, SCH2; 4.75 d, J = 13 Hz and 4.97 d, J = 13 Hz, CH₂OAc; 4.90 d of d, J = 9, 1.6 Hz, CHS; 5.32 d of d, J = 54, 1.6 Hz, CHF. MS: 332.

Step B: Preparation of t-Butyl 3-acetyloxymethyl-7α-fluoro-8-oxo-5-thia-1-azabicyclo[4.2.0]oct-2-ene-2-carboxylate-5,5-dioxide To 182 mg (0.55 mmol) t-Butyl 3-acetyloxymethyl-7α-fluoro-8-oxo-5-thia-1-azabicyclo[4.2.0]-oct-2-ene-2-carboxylate in 20 ml methylene chloride was added 261 mg (1.2 mmol) MCPBA. After stirring 5.5 hours, the mixture was washed with aq K₂HPO₄ and brine, dried with MgSO₄, filtered, evaporated and chromatographed by PLC on silica gel with 1:1 hexane-EtOAc, affording 142 mg t-Butyl 3-acetyloxymethyl-7α-fluoro-8-oxo-5-thia-1-azabicyclo[4.2.0]oct-2-ene-2-carboxylate-5,5-dioxide. NMR (CDCl₃): δ 1.55 s, t-bu; 2.08 s, Ac; 3.73 d, 3.90 d, J = 18 Hz, SO₂CH₂; 4.72 d, 4.90 d, J = 13 Hz, CH₂OAc; 4.86 d of d, J ᴛᴍ 7, 1.6 Hz, CHSO₂; 5.84 d of d, J = 52, 1.6 Hz, CHF.MS: 307, 247.

EXAMPLE 7 t-Butyl 3-acetyloxymethyl-7α-chloro-8-oxo-5-thia-1-azabicyclo[4.2.0]oct-2-ene-2-carboxylate-5,5-dioxide Step A: Preparation of t-Butyl 3-acetyloxymethyl-7α-chloro-5-thia-1-azabicyclo[4.2.0]oct-2-ene-2-carboxylate Following the same procedure as described in Step A, Example 1, 7-AcA t-butyl ester was diazotized to t-Butyl 3-acetyloxymethyl-7-diazo-8-oxo-5-thia-1-azabicyclo[4.2.0]oct-2-ene-2-carboxylate which was taken up into 2 ml EtOH, and treated with 0.1 ml aq HCl. There was an instantaneous vigorous effervescence. After 15 seconds, aq $K_2HPO_4$ and methylene chloride were added. The methylene chloride layer was separated, washed with aq $H_3PO_4$ and brine, dried with $MgSO_4$, filtered and chromatographed by PLC on silica gel, eluting with 25:1 $CHCl_3$-EtOAc, to provide 61 mg pure t-Butyl 3-acetyloxymethyl-7α-chloro-5-thia-1-azabicyclo[4.2.0]oct-2-ene-2-carboxylate. NMR ($CDCl_3$): δ 1.55 s, t-bu; 2.10 s, Ac; 3.40 d, 3.59 d, J=18 Hz, $SCH_2$; 4.79 d, 5.03 d, J=13 Hz, $CH_2OAc$; 4.70 d, J=1.5 Hz, CHS; 4.78 d, J=1.5 Hz, CHCl. MS: 291 $Cl_1$, 231 $Cl_1$.

Step B: Preparation of t-Butyl 3-acetyloxymethyl-7α-chloro-8-oxo-5-thia-1-azabicyclo[4.2.0]oct-2-ene-2-carboxylate-5,5-dioxide 4.5 mq (0.013 mmol) t-Butyl 3-acetyloxymethyl-7α-chloro-5-thia-1-azabicyclo[4.2.0]oct-2-ene-2-carboxylate was stirred with 6.0 mg MCPBA (0.028 mmol) in 0.5 ml methylene chloride for 4 hours. After the first 2 hours, and again after 3.5 hours, 1 mg additional MCPBA was added. The mixture was washed with aq $K_2HPO_4$, dried with $MgSO_4$, filtered and chromatographed on 500 mg silica gel, eluting with 1:1 hexane-EtOAc, 3.2 mg of t-Butyl 3-acetyloxymethyl-7α-chloro-8-oxo-5-thia-1-azabicyclo [4.2.0]oct-2-ene-2-carboxylate-5,5-dioxide. MS: 379 $Cl_1$. NMR ($CDCl_3$): δ 1.57 s, t-bu; 2.08 s, Ac; 3.83 d, 4.00 d, J TM 18, $SO_2CH_2$; 4.69 d, 5.00 d, J =13 Hz, $CH_2OAc$; 4.80 d, J=2 Hz, $CHSO_2$; 5.26 d, J=2 Hz, CHCl.

EXAMPLE 8 t-Butyl 3-hydroxymethyl-7α-methoxy-8-oxo-5-thia-1-azabicyclo[4.2.0]oct-3-ene-2-carboxylate Step A: Preparation of t Butyl 3-acetyloxymethyl-7α-methoxy-8-oxo-5-thia-1-azabicyclo4.2.0]oct-3-ene-2-carboxylate In a 200 ml round bottom flask equipped with a magnetic stirrer were placed t-Butyl 3-acetyloxymethyl-7α-methoxy-8-oxo-5-thio-1-azabicyclo[4.2.0]oct-2-ene-2-carboxylate (7.46 g, 21.7 mmol) chloroform (90 ml) and triethylamine (3.3 ml, 23.6 mmol). The mixture was then heated to reflux for three hours. $^1H$ NMR analysis of an aliquot shows that there was a mixture of isomers (-3-ene and-2-ene) in the approximate ratio of 3:1. The reaction mixture was then evaporated and the brown residue was dried in vacuo. The mixture was then purified by preparative HPLC on a Waters Prep 500 using two silica gel columns in series and hexane:ethyl acetate (3:1) as eluent. The forecut of the partially resolved material was taken and evaporated to give 2.41 g (32%) of pure t-Butyl 3-acetyloxymethyl-7α-methoxy-8-oxo-5-thia-1-azabicyclo[4.2.0]oct-3-ene-2-carboxylate isomer as a yellow oil. $^1H$ NMR ($CDCl_3$): δ 6.45 (4-H, br, s), 5.05 (2-H, br s), 4.90 (7-H, d, J=2), 4.65 (6-H, d, J=2), 4.60 ($CCH_2OAc$, t, J=13 Hz). 3.52 ($OCH_3$, s), 203 ($O_2CCH_3$, s) 1.50 (s, $OC(CH_3)_3$).

Collection of the remainder of the material and evaporation yielded 3 66 g (49%) of a 1:1 mixture of 2-ene and 3-ene isomers as a yellow oil which may be reused in the reaction.

Step B: Preparation of t-Butyl 3-hydroxymethyl-7α-methoxy-8-oxo-5-thia-1-azabicyclo [4.2.0]oct-3-ene-2-carboxylate To a solution of 8.88 g (25.9 mmol) of t-Butyl 3-acetyloxymethyl-7α-methoxy-8-oxo-5-thia-1-azabicyclo[4.2.0]oct-3-ene-2-carboxylate in isopropanol (100 ml) was added Ti(O-ipr)$_4$ (5.4 ml). The reaction mixture was heated to reflux under $N_2$ and monitored by TLC [silica gel using hexane:ethyl acetate (1:1); starting material Rf 0.75, product $R_f$ 0.5] until the starting material had just disappeared The reaction was concentrated and the residue was dissolved in ethyl acetate and washed with 1N aqueous $H_3PO_4$ (50 ml). The aqueous layer was then backwashed with ethyl acetate (50 ml) and the organic layers were combined, washed with water (50 ml) and brine (50 ml). The organic layer was dried over $MgSO_4$ and concentrated to give a yellow oil which was purified using a Waters Prep 500 with hexane:ethyl acetate (2:1) as eluent to give 4.76 g (61%) of a light yellow oil which on standing crystallizes to t-Butyl 3-hydroxymethyl-7α-methoxy-8-oxo-5-thia-1-azabicyclo[4.2.0]oct-3-ene-2-carboxylate. $^1H$ NMR ($CDCl_3$): δ 6.32 (4-H, m); 5.02 (2-H, s); 4.99 (6-H, J=1 Hz), 4.60 (7-H, d J=1 Hz); 4.22 ($CCH_2OH$, br s); 3.53 ($OCH_3$, s); 2.60 (OH, br exch.); 1.50 (—$CO_2C$—($CH_3)_3$, s).

EXAMPLE 9 t-Butyl 3-(3-[hydroxycarbonyl)propanoyloxymethyl-7α-methoxy-8-oxo-5-thia-1-azabicyclo[4.2.0]oct-2-ene-2-carboxylate-5,5-dioxide Step A: Preparation of t-Butyl 3-(3-[hydroxycarbonyl]propanoyloxymethyl-7α-methoxy-8-oxo-5-thia-1-azabicyclo[4.2.]oct-3-ene-2-carboxylate A mixture of t-Butyl 3-hydroxymethyl-7α-methoxy-8-oxo-5-thia-1-azabicyclo [4.2.0]oct-3-ene-2-carboxylate (602 mg, 2.0 mmol) and succinic anhydride (300 mg, 3.0 mmol) were dissolved in dry tetrahydrofuran (4 ml) under nitrogen at room temperature, then 4-[N,N-dimethylamino]pyridine (300 mg, 2.5 mmol) was added with stirring. A solid began to separate out shortly after mixing The mixture was allowed to stir 15 hours, then 50% saturated aqueous sodium bicarbonate (10 ml) was added, and the mixture was extracted with ether (2×20 ml). The combined ether extracts were washed with 50% sat. aq $NaHCO_3$ (10 ml), then the aqueous extracts were combined and acidified to pH 2.5 (using 1.0 M.$H_3PO_4$), the resulting cloudy solution was extracted with ethyl acetate (2×30 ml), then the organic layers were combined and washed with saturated brine (25 ml) and dried over $Na_2SO_4$. The solvent was removed in vacuo to give t-Butyl 3-hydroxycarbonylethyl-carbonyloxymethyl-7α-methoxy-8-oxo-5-thia-1-azabicyclo[4.2.0]oct-3-ene-2-carboxylate a yellow oil. This material was sufficiently pure to be carried on to the next step.

Step B: Preparation of t-Butyl 3-(3-[hydroxycarbonyl]propanoyloxymethyl)-7α-methoxy-8-oxo-5-thia-1-azabicyclo[4.2.0]oct-2-ene-2-carboxylate-5,5-dioxide The crude product t-Butyl 3-hydroxycarbonylethylcarbonyloxymethyl-7α-methoxy-8-oxo-5-thia-1-azabicyclo[4.2.0]oct-3-ene-2-carboxylate from the above reaction was dissolved in methylene chloride (10 ml) and cooled to 0° under $N_2$. Then metachloroperbenzoic acid (1.0 g, 5 mmol assuming 85% purity) was added all at once, and after stirring for 5 minutes, the cooling bath was removed Stirring was continued for five hours, then the reaction mixture was filtered and the filter cake was washed with ice-cold $CH_2Cl_2$ (5 ml). The combined filtrates were evaporated and the residue was dissolved in $CH_2Cl_2$/EtOAc (3:1) (8 ml) and chromatographed on silica gel (4×[20 cm×20 cm] 2000 μ silica gel GF using 1% HOAc in 1/1 EtOAc/Hex as eluent) the bands at $R_f$0.3 were removed, combined and eluted with 1% HOAc in EtOAc, and the eluent was evaporated to give a clear oil. This material was lyophilized from benzene to remove HOAc, then crystallized from ether/hexane to Yield 502 mg of product t-Butyl 3-(3-[hydroxycarbonyl]propanoyloxymethyl)-7α-methoxy-8-oxo-5-thia-1-azabicyclo-[4.2.0]oct-2-ene-2-carboxylate-5,5-dioxide (58%) m.p. 112°–113°.

EXAMPLE 10 t-Butyl 3-hydroxycarbonylmethylaminocarbonyloxymethyl-7α-methoxy-8-oxo-5-thia-1-azabicyclo[4.2.0]oct-2-ene-2-carboxylate-5,5-dioxide

Step A: Preparation of t-Butyl-3-(p-methoxybenzyloxy) Carbonylmethylaminocarbonyloxymethyl-7α-methoxy-8-oxo-5-thia-1-azabicyclo[4.2.0]oct-3-ene-2-carboxylate To a solution of t-Butyl 3-hydroxymethyl-7α-methoxy-8-oxo-5thia-1-azabicyclo [4.2.0]oct-3-ene-2-carboxylate (602 mg, 2.0 mmol) in methylene chloride (5 ml) was added N,N'-carbonyl diimidazole (324 mg, 2.0 mmol). The resulting solution was stirred at room temperature for thirty minutes, then the solvent was removed in vacuo and the residue was dissolved in N,N-dimethylformamide (5 ml). Then glycine P-methoxybenzylester hydrochloride (693 mg, 3.0 mmol) and 4-(N'N-dimethylamino)pyridine (366 mg, 3.0 mmol) were added, and the resulting mixture was stirred for 18 hours. The reaction mixture was then poured into water (30 ml) and extracted with ethyl acetate (2×30 ml). The combined organic layers were washed with water (20 ml) and saturated brine (20 ml), then dried over sodium sulfate, and the solvent was removed to give a residue which was purified by chromatography (4×[20 cm×20 cm] 2000 μ silica gel GF plates, developed in ethyl acetate/hexane [1/1]. The bands at $R_f$ 0.55 were removed and eluted with ethyl acetate to produce 508 mg (51%) of t-Butyl-3-(p-methoxybenzyloxy)carbonylmethylaminocarbonyloxymethyl-7α-methoxy-8-oxo-5-thia-1-azabicyclo[4.2.0]oct-3-ene-2-carboxylate. $^1$H NMR (CDCl$_3$) δ 7.25–6.85 (C$_6$H$_4$OCH$_3$, d, d, J=9Hz); 6.40 (C=C(H)S—, br. s); 5.40 (=NH, br, s); 5.18 (—C$_6$H$_4$—CH$_2$—,s); 5.05 (—CH—CH⊙CH), s); 4.90 (C-6H, d, J=2Hz); 4.70 (C-7H, d, J=Hz); 4.65 (C-3-CH$_2$, t, J=12Hz); 3.95 (—HN—CH$_2$CO—, d, J=6 Hz); 3.80 (—C$_6$H$_4$—OCH$_3$, s); 3.55 (C-7-OCH$_3$, s); 1.55 [—COO—C(CH$_3$)$_3$].

Step B: Preparation of t-Butyl 3-(p-methoxybenzyloxy) carbonylmethylaminocarbonyloxymethyl-7α-methoxy-8-oxo-5-thia-1-azabicyclo[4.2.0]oct-2-ene-2-carboxylate-5,5-dioxide Following substantially the same procedures as described in Example 9, Step B, 278 mg (0.56 mmole) of t-Butyl-3-(p-methoxybenzyloxy)carbonylmethylaminocarbonyloxymethyl-7α-methoxy-8-oxo-5-thia-1-azabicyclo[4.2.0]oct-3-ene-2-carboxylate was oxidized to t-Butyl-3-(p-methoxybenzyloxy)carbonylmethylaminocarbonyloxymethyl-7α-methoxy-8-oxo-5-thia-1-azabicyclo[4.2.0]oct-2-ene-2-carboxylate-5,5-dioxide. (226 mg, 76%) as a glass. $^1$H NMR δ (CDCl$_3$) 7.28–6.85 —C$_6$H$_4$OCH$_3$, d, d, J=9); 5.55 ( —CONH—, br t, J=6); 5.19 (C-6 or 7H, d, J=2); 5.10 (—C$_6$H$_8$—CH$_2$O—; s); 4.85 (C—3—CH$_2$O—), d of cl, J=12, 26); 3.90 (C$_2$—CH$_2$, —4N—CH$_2$COO—, m); 3.79 (—C$_6$H$_4$—OCH$_3$, s); 3.55 (C-7(OCH$_3$), s); 1.55 (—CO$_2$C(CH$_3$)$_3$, s).

Step C: Preparation of t-Butyl 3-hydroxycarbonyl-methylaminocarbonyloxymethyl-7α-methoxy-8-oxo-5-thia-1-azabicyclo[4.2.0]oct-2-ene-2-carboxylate-5,5-dioxide A mixture of trifluoroacetic acid and anisole (5:1) was cooled to 0°, then one milliliter of this solution was added to a flask under $N_2$ at 0° containing t-butyl 3-(p-methoxybenzyloxy)carbonylmethylaminocarbonyloxymethyl-7α-methoxy-8-oxo-5-thia-1-azabicyclo[4.2.-0]oct-2-ene-2-carboxylate-5,5-dioxide (105 mg, 0.2 mmol). The mixture was stirred vigorously with cooling until it becomes homogeneous. Stirring was continued for 2 minutes, then the flask was attached through a gas inlet tube to a vacuum pump in order to remove solvent as fast as possible with continued cooling. Cooling was maintained until the reaction mixture becomes noticeably viscous. The cooling bath was removed and pumping was continued for one hour, then the residue was dissolved in a methylene chloride (one ml) and chromatographed (20×20 cm 2000 μ silica gel GF plate using 1% HOAc in ethylacetate/hexane (1/1) as eluent). The band at $R_f$0.25 was removed and eluted with 1% HOAc in ethyl acetate. The solvent was removed and the residue was lyophilized from benzene to remove residual HOAc to obtain t-Butyl 3-hydroxycarbonylmethylaminocarbonyloxymethyl- 7α-methoxy-8-oxo-5-thia-1-azabicyclo[4.2.0]oct-2-ene-2-carboxylate-5,5-dioxide as an amorphous solid (36 mq, 44% yield) $^1$H NMR (CDCl$_3$); δ 6.95 (CO$_2$H, br exch.); 5.60 (—CONHCH$_2$—, br exch.); 5.20 (C$_6$ or C$_7$ H, J=2); 5.90

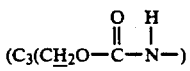

br d of d, J=12, 22) 5.78 (C$_6$ or C$_7$ H, br s .90 (C$_4$-H and HNCH$_2$COOH, m); 3.55 (C$_7$(OCH$_3$), s); 1.55 (CO$_2$C(CH$_3$, s).

EXAMPLE 11 t-Butyl 3-hydroxycarbonyl-7α-methoxy-8-oxo-5-thia-1-azabicyclo[4.2.0]oct-2-ene-2-carboxylate-5,5-dioxide Step A: Preparation of t-Butyl 3-formyl-7α-methoxy-8-oxo-5-thia-1-azabicyclo[4.2.0]oct-2-ene-2carboxylate To a 100 ml recovery flask under nitrogen was added solution of t-Butyl 3-hydroxymethyl-7α-methoxy-8-oxo-5-thia-1-azabicyclo[4.2.0]oct-3-ene-2-carboxylate (300 mg 1.0 mmol) in acetone (26 ml-freshly distilled from Jones' Reagent). The solution was then cooled to 0°, and Jones Reagent (1.0 mmol, 372 μl of a 2.7 M solution) was added slowly with stirring. There was an immediate color change from yellow to green with precipitate formation After the addition was complete, stirring was continued for ten minutes, then it was poured into water (100 ml) and stirred The resulting green solution was extracted with ethyl acetate (4×30 ml), and the combined organic extracts were washed with brine, then dried with sodium sulfate. The solvent was removed to give a yellow oil (264 m ) which was purified by chromatography (2000 μ silica gel GF prep plate [20×20 cm] using ethyl acetate:hexane (1:1) as eluent). The band of $R_f$ 0.5 was removed to give 214 mg (72%) of t-Butyl 3-formyl-7α-methoxy-8-oxo-5-thia-1-azabicyclo[4.2.0]oct-3-ene-2-carboxylate as a clear oil which solidified on cooling. $^1$H NMR (CDCl$_3$): δ 9.40 (—CHO, s); 7.55 (C$_4$-H, d, J=1 Hz); 5.30 (C$_6$ or C$_7$-H, d, J=1); 5.08 (C$_2$-H, d, J TM 1); 4.65 (C$_6$ or C$_7$-H, d, J TM 1); 3.55 (C$_7$(OCH$_3$), s); 1.55 (CO$_2$C(CH$_3$)$_3$m s).

Step B: Preparation of t-Butyl 3-hydroxycarbonyl-7α-methoxy-8-oxo-5-thia-1-azabicyclo[4.2.0]oct-3-ene-2-carboxylate-5-dioxide Into a 100 ml recovery flask under nitrogen was placed a solution of t-Butyl 3-formyl-7α-methoxy-8-oxo-5-thia-1-azabicyclo[4.2.0]oct-3-ene-2-carboxylate (425 mg, 1.42 mmol) in acetone distilled from Jones' Reagent (35 ml). To this solution was added Jones' Reagent (1.6 ml of a 2.7 M solution, 4.2 mmol) dropwise over 15 minutes Stirring was continued for three hours, then the reaction was diluted with water (100 ml) and the resulting green solution was extracted with ethyl acetate (2×75 ml). The combined organic extracts were washed with saturated brine (50 ml) and dried over magnesium sulfate. The solvent was removed in vacuo to give a yellow oil which was purified by silica gel prep plate chromatography (2×2000 μ using 1% HOAc in ethyl acetate/hexane [1/1]). The band at RF 0.3 is removed and eluted to give 196 mg (44%) of t-butyl 3-hydroxycarbonyl-7α-methoxy-8-oxo-5-thia-1-azabicyclo [4.2.0]oct-3-ene-2-carboxylate as a clear oil. $^1$H NMR (CDCl$_3$); 9.90 (CO$_2$H, br, s, exch.); 7.72 (C$_4$-H, d, J=1.5 Hz); 5.3 (C$_6$ or C$_7$-H, d, J=1), 4.95 (C$_2$—H, br, s); 4.65 C$_7$—H, d, J=1); 3.55 (C$_6$(OCH$_3$), s); 1.50 (CO$_2$C(CH$_3$)$_3$, s).

Following substantially the same procedure as described in Example 9, Step B, t-Butyl 3-hydroxy-carbonyl-7α-methoxy-8-oxo-5-thia-1-azabicyclo[4.2.0]oct-3-ene-2-carboxylate (196 mg, 0.62 mmol) was oxidized to afford 96 mg (46%) of t-Butyl 3-hydroxycarbonyl-7α-methoxy-8-oxo-5-thia-1-azabicyclo[4.2.0]oct-2-ene-2-carboxylate-5,5-dioxide as a white solid. $^1$H NMR (CDCl$_3$); δ 8.65 (CO$_2$H, br, s); 5.30 (C$_6$ or C$_7$-H, d, J TM 3 Hz); 5.05 (C$_6$ or C$_7$—H, br, d, J=3); 4.05 (C$_4$—H$_2$, br, s); 3.55 (C$_7$(OCH$_3$), s); 1.58 (CO$_2$C(CH$_3$)$_3$,s).

EXAMPLE 12 t-Butyl 3-chloromethyl-7α-methoxy-8-oxo-5-thia-1-azabicyclo[4.2.0]oct-2-ene-2-carboxylate-5,5-dioxide Step A: Preparation of t-Butyl 3-chloro-methyl-7α-methoxy-8-oxo-5-thia-1-azabicyclo[4.2.0]oct-3-ene-2-carboxylate To a solution of 0.9 g (3 mmol) of t-Butyl 3-hydroxymethyl-7α-methoxy-8-oxo-5-thia-1-azabicyclo [4.2.0]oct-3-ene-2-carboxylate in 20 ml of tetrahydrofuran was added 1 ml of pyridine. Thionyl chloride (0.5 ml) was added dropwise over 5 min. After stirring the reaction mixture for 0.5 hours, it was poured into ice-cold water and extracted with ethyl acetate. The combined extract was washed with 7% sodium bicarbonate solution, brine and dried over sodium sulfate. The concentrated filtrate was flash chromatographed with 10% ethyl acetate-hexane to yield 0.626 g (65%) yield of t-butyl 3-chloromethyl-7α-methoxy-8-oxo-5-thia-1-azabicyclo[4.2.0]oct-3-ene-2-carboxylate as a pale yellow solid. m.p. 85°.

Step B: Preparation of t-Butyl 3-chloromethyl-7α-methoxy-8-oxo-5-thia-1-azabicyclo[4.2.0]oct-2-ene-2-carboxylate-5,5-dioxide Following substantially the same procedures as described in Example 9, Step B, 0.32 g (1 mmol) of t-Butyl 3- chloromethyl-7α-methoxy-8-oxo-5-thia-1-azabicyclo[4 2.0]oct-3-ene-2-carboxylate was oxidized to afford 0.301 g (86% yield) of t-Butyl 3- chloromethyl-7α-methoxy-8-oxo-5-thia-1-azabicyclo[4.2.0]-oct-2-ene-2-carboxylate-5,5-dioxide, m.p. 132° C.

EXAMPLE 13 t-Butyl 3-phenylthio (or 3-phenylsulfonyl)methyl-7α-methoxy-8-oxo-5-thia-1-azabicyclo[4.2.0]oct-2-ene-2-carboxylate-5,5-dioxide Step A: Preparation of t-Butyl 3-phenylthiomethyl-7α-methoxy-8-oxo-5-thia-1-azabicyclo[4.2.0]oct-2-ene-2-carboxylate-5,5-dioxide A solution of 35 mg (0.24 mmol) of potassium thiophenoxide in 0.5 ml of water was added to a solution of 83 mg (0.24 mmol) of t-Butyl 3- chloromethyl-7α-methoxy-8-oxo-5-thia-1-azabicyclo[4.2.0]-oct-2-ene-2-carboxylate-5,5-dioxide in 2 ml of acetone. After stirring the reaction mixture for 40 hours it was concentrated in vacuo. The residue was dissolved in ethyl acetate and poured into 7% sodium bicarbonate solution. The layers were separated and the aqueous layer was extracted with ethyl acetate. The combined organic layer was washed with brine and dried over sodium sulfate. The concentrated filtrate was chromatographed on a preparative silica gel plate using 20% ethyl acetate-hexane to obtain 66 mg (66% yield) of t-butyl 3-phenylthiomethyl-7α-methoxy-8-oxo-5-thia-1-azabicyclo[4.2.0]oct-2-ene-2-carboxylate-5,5-dioxide NMR(CDCl$_3$): δ 1.45 (s, 9), 3.46 (s, 3), 3.58 (d, 1, 14 Hz), 3.62 (d, 1, 18 Hz), 4.08 (d, 1, 18 Hz), 4.18 (d, 1, 14 Hz), 4.4 (bs, 1), 5.02 (d, 1, 2 Hz), 7.1–7.4 (m, 5). (continued)

Step B: Preparation of t-Butyl 3-phenylsulfinylmethyl or 3-phenylsulfonylmethyl-7α-methoxy-8-oxo-5-thia-1-azabicyclo[4.2.0]oct-2-ene-2-carboxylate-5,5-dioxide A solution of 40 mg (90%, 0.21 mmol) of m-chloroperbenzoic acid in 1 ml of dichloromethane was added to a solution of 60 mg (0.14 mmol) of t-Butyl 3-phenylthiomethyl-7α-methoxy-8-oxo-5-thia-1-azabicyclo[4.2.0]oct-2-ene-2-carboxylate-5,5-dioxide while cooling in an ice bath. The reaction mixture was stirred for 0.5 hour as it warmed to room temperature The solution was poured into 7% sodium bicarbonate solution containing excess sodium sulfite and extracted with dichloromethane. The combined dichloromethane layers was washed with brine and dried over sodium sulfate. The concentrated filtrate was chromatographed on a preparative silica gel plate with 50% ethyl acetate-hexane to give two bands. The less polar band yielded 32 mg (50% yield) of t-Butyl 3-phenylsulfonylmethyl-7α-methoxy-8-oxo-5-thia-1-azabicyclo[4.2.0]oct-2-ene-2-carboxylate-5,5-dioxide. NMR(CDCl$_3$): δ 1.46 (s, 9), 3.52 (s, 3), 3.81 (d, 2, 14 Hz), 3.82 (d, 2, 18 Hz), 4.32 (d, 1, 18Hz), 4.74 (d, 1, 14 Hz), 4.76 (bs, 1), 5.09 (d, 1, 2 Hz), 7.2–7.9 (m, 5). The more polar band yielded 27 mq (44% yield) of t-Butyl 3-phenylsulfinylmethyl-7α-methoxy-8-oxo-5-thia-1-azabicyclo[4.2.0]oct-2-ene-2-carboxylate-5,5-dioxide. NMR(CDCl$_3$): δ 1.51 (s, 9), 3.53 (s, 3), 3.3–4.1 (m, 4), 4.53 (bs, 0.5), 4.67 (bs, 0.5), 5.07 (d, 1, 2 Hz), 7.3–7.7 (m, 5).

EXAMPLE 14 t-Butyl 3-methoxymethyl-7α-methoxy-8-oxo-5-thia-1-azabicyclo[4.2.0]oct-2-ene-2-carboxylate-5,5-dioxide A solution of 30 mg (0.09 mmol) of t-butyl 3-chloromethyl-7α-methoxy-8-oxo-5-thia-1-azabicyclo[4.2.0]oct-3-ene-2-carboxylate in 1 ml of methanol was stirred at room temperature for 16 hours. The solution was concentrated in vacuo and the residue was chromatographed on a short silica gel column with 20% ethyl acetate-hexane to obtain 21 mg t-butyl 3-methoxymethyl-7α-methoxy-8-oxo-5-thia-1-azabicyclo[4.2.0]oct-3-ene-2-carboxylate. NMR (CDCl$_3$): δ 3.25 (s, 1.5) 3.39 (s, 1.5), 6.23 (bs, 0.5).

Following substantially the same procedure as described in Example 9, Step B, 21 mg of t-butyl 3-methoxymethyl-7α-methoxy-8-oxo-5-thia-1-azabicyclo[4.2.0]oct-3-ene-2-carboxylate was oxidized to obtain 11 mg (34% yield) of t-butyl 3-methoxymethyl-7α-methoxy-8-oxo-5-thia-1-azabicyclo[4.2.0]oct-2-ene'-2-carboxylate-5,5-dioxide. NMR (CDCl$_3$): δ 1.53 (s, 9), 3.27 (s, 3), 3.53 (s, 3), 3.72 (ABq, 2, 17 Hz), 4.14 (s, 2), 4.6 (bs, 1), 5.05 (d, 1, 2 Hz).

EXAMPLE 15 t-Butyl 3-methyl-7α-methoxy-8-oxo-5-thia-1-azabicyclo[4.2.0]oct-2-ene-2-carboxylate-5,5-dioxide To a solution of 5 g (14.0 mmol) of t-butyl-3-acetyloxymethyl-7α-methoxy-8-oxo-5-thia-1-azabicyclo[4.2.0]oct-2-ene-2-carboxylate in 100 ml of ethanol was added 15 g of 10% palladium on carbon under a nitrogen atmosphere. The solution was hydrogenated on a Parr apparatus for 3 hr. The reaction mix was filtered and the catalyst was thoroughly washed with warm methanol The filtrate and washings were combined and concentrated in vacuo. The residue was flash-chromatographed using 20% ethylacetate-hexane to obtain 1.97 g (47% yield) of t-butyl 3-methyl-7α-methoxy-8-oxo-5-thia-1-azabicyclo[4.2.0]oct-2-ene-2-carboxylate. NMR CDCl$_3$): δ 1.53 (s, 9H), 2.01 (s, 3), 3.27 (ABq, 2, 18 Hz), 3.52 (s, 3), 4,4 (d, 1, 2 Hz), 4.6 (d, 1, 2 Hz).

Following substantially the same procedure as described in Example 1, Step C 11 mg (0.04 mmol) of t-butyl-3-methyl-7α-methoxy-8-oxo-5-thia-1- o azabicyclo[4.2.0]oct-2-ene-2-carboxylate was oxidized to obtain 6 mg (48% yield) of t-Butyl 3-methyl-7α-methoxy-8-oxo-5-thia-1-azabicyclo[4.2.0]oct-2-ene-2-carboxylate-5,5-dioxide. NMR (CDCl$_3$): δ 1.53 (s, 9), 2.0 (s, 3), 3.53 (s, 3), 3.6 (ABq, 2, 12 Hz), 4.54 (bs, 1), 5.05 (bs, 1).

EXAMPLE 16 m-Methoxycarbonylbenzyl-3-acetyloxymethyl-7α-methoxy-8-oxo-5-thia-1-azabicyclo[4.2.0]oct-2-ene-2-carboxylate-5-dioxide

Step A: Preparation of N,N'-diisopropyl-0-(m-methoxycarbonylbenzyl)-isourea A mixture of 4.75 g (28.6 mmols) of m-methoxycarbonylbenzyl alcohol and 3.6 g (28.6 mmols) of N,N'-diisopropylcarbodiimide was stirred with 50 mg (0.51 mmols) of cuprous chloride at room temperature for 24 hours. The reaction was then diluted with 10 ml of hexane and eluted through a short column of neutral alumina with 20% ethyl acetate-hexane to give 8.0 g (96%) of N,N'-diisopropyl-0-(m-methoxycarbonylbenzyl)-isourea as a colorless oil.

Step B: Preparation of m-methoxycarbonyl-benzyl-3-acetyloxymethyl-7α-methoxy-8-oxo-5-thia-1-azabicyclo[4.2.0]oct-2-ene-2-carboxylate A solution of 1.0 g (3.4 mmole) of N,N'-diisopropyl-O-(m-methoxycarbonylbenzyl)-isourea and 1.0 g (3.4 mmole) of 3-acetyloxymethyl-7α-methoxy-8-oxo-5-thia-1-azabicyclo[4.2.0]oct-2-ene-2-carboxylic acid in 2.0 ml of tetrahydrofuran (THF) was stirred for 24 hours at room temperature. The reaction was then cooled to −10° C., filtered and concentrated in vacuo. The product was purified by flash chromatography using a solvent gradient of 35 to 40% ethyl acetate-hexane to give 300 mg (20%) of m-methoxycarbonylbenzyl 3-acetyloxymethyl-7α-methoxy-8-oxo-5-thia-1-azabicyclo[4.2.0]oct-2-ene-2-carboxylate as an oil, NMR (CDCl$_3$); δ 2.04 (s, 3), 3.40 (ABq, 2, 18 Hz) 3.50 (s, 3), 3.87 (s, 3), 4.47 (d, 1, 2 Hz), 4.63 (d, 2, 2 Hz), 4.78 (ABq, 2, 13 Hz), 5.27 (ABq, 2, 13 Hz), 7.2–7.6 (m, 2), 7.7–8.0 (m, 2).

Step C: Preparation of m-methoxycarbonylbenzyl-3-acetyloxymethyl-7α-methoxy-B-oxo-5-thia-1-azabicyclo[4.2.0]oct-2-ene-2-carboxylate-5,5-dioxide Following the same procedure as described in Example 1, Step C, 250 mg (0.57 mmole) of m-methoxycarbonylbenzyl 3-acetyloxymethyl-7α-methoxy-8-oxo-5-thia-1-azabicyclo[4.2.0]oct-2-ene-2-carboxylate was oxidized to 210 mg (78%) of M-methoxycarbonylbenzyl 3-acetyloxymethyl-7α-methoxy-8-oxo-5-thia-1-azabicyclo [4.2.0]oct-2-ene-2-carboxylate-5,5-dioxide, NMR (CDCl$_3$); δ 2.03 (s, 3), 3.52 (s, 3), 3.87 (ABq, 2, 19 Hz), 3.90 (s, 3), 4.67 (d, 1, 2 Hz), 4.80 (ABq, 2, 14 Hz), 5.11 (d, 1, 2 Hz), 5.30 (br s, 2), 7.1–7.6 (m, 2), 7.8–8.1 (m, 2).

Following substantially the same procedure as described above but substituting for the N,N'-diisopropyl-O-(m-methoxycarbonylbenzyl)-isourea used therein N,N'-diisopropyl-O-(p-(p-methoxybenzyloxy) carbonylbenzyl)-isourea, there was prepared p-(p-methoxybenzyloxy)carbonylbenzyl 3-acetyloxymethyl-7α-methoxy-8-oxo-5-thia-1-azabicyclo[4.2.0]oct-2-ene-2-carboxylate as an oil, NMR (CDCl$_3$): δ 2.02 (s, 3), 3.42 (ABq, 2, 19 Hz), 3.53 (s, 3), 3.73 (s, 3), 4.44 (d, 1, 2 Hz), 4.62 (d, 1, 2 Hz), 4.80 (ABq, 2, 13 Hz), 5.27 (ABq, 2, 13 Hz), 6.7–8.1 (m, 8).

Subsequently, following the same procedure as described above, 80 mg (0.15 mmols) of the above ester was oxidized to give 40 mg (47%) of p-(p-methoxybenzyloxy)carbonylbenzyl 3-acetyloxymethyl-7α-methoxy-8-oxo-5-thia-1-azabicyclo[4.2.0]oct-2-ene- 2-carboxylate-5,5-dioxide as an oil, NMR (CDCl$_3$); δ 2.03 (s, 3), 3.53 (s, 3), 3.81 (ABq, 2, 18 Hz), 4.4–5.2 (m, 4), 5.26 (br s, 2), 6.7–8.1 (m, 8).

EXAMPLE 17 p-Hydroxycarbonylbenzyl 3-acetyloxymethyl-7α-methoxy-8-oxo-5-thia-1-azabicyclo[4.2.0]oct-2-ene-2-carboxylate-5,5-dioxide A solution of 35 mg (0.061 mmols) of p-(p-methoxybenzyl)oxycarbonylbenzyl 3-acetyloxymethyl-7α-methoxy-8-oxo-5-thia-1-azabicyclo[4.2.0]oct-2-ene'-2-carboxylate-5,5-dioxide in 0.8 ml of trifluoroacetic acid was stirred with 0.2 ml of anisole at 0° C. for 15 minutes. The reaction was concentrated in vacuo and the residue was purified on a 1000 μ silica preparative plate using 1% acetic acid in 50% ethyl acetate-hexane as solvent to give 24 mg (87%) of p-hydroxycarbonylbenzyl 3-acetyloxymethyl-7α-methoxy-8-oxo-5-thia-1-azabicyclo[4.2.0]oct-2-ene-2-carboxylate-5,5-dioxide as a white solid, NMR (CDCl$_3$): δ 2.02 (s, 3), 3.53 (s, 3), 3.83 (ABq, 2, 10 Hz), 4.67 (br s, 1), 4.83 (ABq, 2, 14 Hz), 5.12 (d, 1, 2 Hz), 5.33 (br s, 2), 7.68 (ABq, 4, 8 Hz).

EXAMPLE 18

Ethoxycarbonylmethyl 3-acetyloxymethyl-7α-methoxy-8-oxo-5-thia-1-azabicyclo[4.2.0]oct-2-ene-2-carboxylate-5,5-dioxide A solution of 1.0 g (3.5 mmols) of 3-acetyloxymethyl-7α-methoxy-8-oxo-5-thia-1-azabicyclo[4.2.0]oct-2-ene-2-carboxylic acid and 4 ml of ethyl diazoacetate in 25 ml of methylene chloride was stirred with 10 mg of rhodium (II) acetate dimer at 35° C. for 30 minutes The reaction was then concentrated in vacuo and the residue was purified by flash chromatography on silica gel eluting with 40–50% ethyl acetate-hexane. The fractions containing the product are combined, evaporated and rechromatographed using 10% ethyl acetate-methylene chloride as eluant to give 250 mg (34%) of ethoxycarbonylmethyl 3-acetyloxymethyl-7α-methoxy-8-oxo-5-thia-1-azabicyclo[4.2.0]-oct-2-ene-2-carboxylate, NMR (CDCl$_3$) 2.37 (t, 3, 7 Hz), 2.06 (s, 3), 3.43 (ABq, 2, 19 Hz), 3.53 (s, 3), 4.20 (q, 2, 7 Hz), 4.43 (d, 1, 2 Hz), 4.63 (d, 1, 2 Hz), 4.73 (ABq, 2, 16 Hz), 4.87 (ABq, 2, 13 Hz).

Following the same procedure as described in Example 1, Step C, 250 mg (0.67 mmols) of the resulting ethoxycarbonylmethyl ester was oxidized to give 190 mg (69%) of ethoxycarbonylmethyl 3-acetyloxymethyl-7α-methoxy-8-oxo-5-thia-1-azabicyclo[4.2.0]oct-2-ene-2-carboxylate-5,5-dioxide, NMR (CDCl$_3$); δ 1.29 (t, 3, 7 Hz), 2.07 (s, 3), 3.57 (s, 3), 3.89 (ABq, 2, 18 Hz), 4 18 (t, 2, 7 Hz), 4.74 (m, 3), 4.89 (ABq, 2, 14 Hz), 5.11 (d, 1, 2 Hz).

EXAMPLE 19 t-Butoxycarbonylmethyl 3-acetyloxymethyl-7α-methoxy-8-oxo-5-thia-1-azabicyclo[4.2.0]oct-2-ene-2-carboxylate-5,5-dioxide A solution of 500 mg (1.7 mmols) 3-acetyloxy-methyl-7α-methoxy-8-oxo-5-thia-1-azabicyclo[4.2.1]-oct-2-ene-2-carboxylic acid in 2 ml of N,N-dimethylacetamide was stirred with 300 mg (3.4 mmols) of sodium bicarbonate and 525 mg (3.4 mmoles) of α-butyl chloroacetate at room temperature for 16 hours. The reaction was diluted with water and extracted with methylene chloride. The organic layer was washed with water and saturated aqueous sodium chloride solution dried over sodium sulfate and evaporated in vacuo. The residue was chromatographed on silica gel to give 20 mg of the t-butoxycarbonylmethyl ester as a mixture of 3-ene- and 2-ene-isomers which was oxidized directly, by following the procedure described in Example 1, Step C, to give 7 mg of t-butoxycarbonylmethyl 3-acetyloxymethyl-7α-methoxy-8-oxo-5-thia-1-azabicyclo[4.2.0]oct-2-ene-2-carboxylate-5,5-dioxide as an oil, NMR (CDCl$_3$); δ 1.48 (s, 9), 2.07 (s, 3), 3.51 (s, 3), 3.85 (AB, 2, 18 Hz), 4.5–5.0 (m, 5), 5.11 (d, 1, 2 Hz).

EXAMPLE 20

N-Benzyl-N-methyl 3-acetyloxymethyl-7α-methoxy-8-oxo-5-thia-1-azabicyclo[4.2.0]oct-2-ene-2-carboxamide-5,5-dioxide A solution of 2.0 g (7.0 mmol) of 3-acetyloxymethyl-7α-methoxy-8-oxo-5-thia-1-azabicyclo[4.2.0]oct-2-ene-2-carboxylic acid in 10 ml of dioxane and 20 ml of acetone was stirred with 1.0 g (7.0 mmols) of isobutyl chloroformate and 600 μl (7.0 mmols) of pyridine at −15° C. After 20 minutes 2.5 g (21 mmoles) of N-methylbenzylamine was added and the reaction is stirred at −15° C. for 1 hour, then allowed to warm to room temperature for 2 hours The reaction was quenched with dilute hydrochloric acid and extracted into methylene chloride. The organic layer was washed with saturated aqueous sodium bicarbonate solution and saturated aqueous sodium chloride solution, dried over sodium sulfate and evaporated. The residue was chromatographed on silica gel to give 280 mg (10%) of N-benzyl-N-methyl 3-acetyloxymethyl-7α-methoxy-8-oxo-5-thia-1-azabicyclo-[4.2.0]oct-2-ene-2-carboxamide, NMR(CDCl$_3$): 1.97 and 2.00 (s, 3), 2.83 and 2.90 (s, 3), 3.0 to 3.7 (m, 5), 4.3 to 4.8 (m, 6), 7.3 (br s, 5).

Following similar procedures as described in Example 1, Step C, 275 mg (0.71 mmoles) of N-benzyl-N-methyl 3-acetyloxymethyl-7α-methoxy-8-oxo-5-thia-1-azabicyclo[4.2.0]oct-2-ene-2-formamide was oxidized to give 170 mg (57%) of N-benzyl-N-methyl 3-acetyloxymethyl-7α-methoxy-8-oxo-5-thia-1-azabicyclo[4.2.0]-oct-2-ene-2-carboxamide-5,5-dioxide, NMR(CDCl$_3$): δ 1.97 and 2.00 (s, 3), 2.78 and 2.89 (s, 3), 3.4–4.1 (m, s), 4.3–4.8 (m, 5), 5.10 (d, 1, 2 Hz), 7.22 (br s, 5).

EXAMPLE 21

N-(t-Butoxycarbonyl)methyl 3-acetyloxymethyl-7α-methoxy-8-oxo-5-thia-1-azabicyclo[4.2.0]oct-2-ene-2-carboxamide-5,5-dioxide A solution of 1.0 g (3.4 mmoles) of 3-acetyloxymethyl-7α-methoxy-8-oxo-5-thia-1-azabicyclo[4.2.0]oct- 2-ene-2-carboxylic acid in 25 ml of methylene chloride was stirred with 1.1 g (5.1 mmole) of dicyclohexylcarbodiimide and 450 mg (3.4 mmols) of tert-butyl glycinate at room temperature for 4 hours. The reaction was concentrated in vacuo and the residue was eluted through a short column of silica gel using 50–60% ethyl acetate-hexane. The fractions containing the resulting amide were combined and evaporated. The residue was further purified by chromatography on silica gel to give 230 mg (17%) of N-(t-butoxycarbonyl)methyl 3-acetyloxymethyl-- 7α-methoxy-8-oxo-5-thia-1-azabicyclo[4.2.0]-oct-2-ene-2-carboxamide, NMR(CDCl$_3$): δ 1.46 (s, 9), 2.07 (s, 3), 3.1–3.6 (m, 2), 3.50 (s, 3), 3.8–4.1 (m, 2), 4.47 (br s, 1), 4.63 (br s, 1), 4.87 (ABq, 2, 13 Hz), 7.4 (br s, 1).

Following similar procedures as described in Example 1, Step C, N-(t-butoxycarbonyl)methyl 3-acetyloxymethyl-7α-methoxy-8-oxo-5-thia-1-azabicyclo-[4.2.0]oct-2-ene-2-carboxamide was oxidized to give 60 mg of N-(t-butoxycarbonyl)methyl 3-acetyloxymethyl-7α-methoxy-8-oxo-5-thia-1-azabicyclo[4.2.0]oct-2-ene-2-carboxamide-5,5-dioxide, NMR(CDCl$_3$): δ 1.47 (s, 9), 2.07 (s, 3), 3.50 (s, 3), 3.5–4.1 (m, 4), 4.4–4.9 (m, 3), 5.07 (d, 1, 2 Hz), 7.3 (br s, 1).

EXAMPLE 22

Benzyl 3-acetyloxymethyl-7α-methoxy-8-oxo-5-thia-1-azabicyclo[4.2.0]oct-2-ene-2-carboxylate-5,5-dioxide Trifluoroacetic acid (5 ml) was added to 316 mg (0.92 mm) of t-butyl 3-acetyloxymethyl-7α-methoxy-8-oxo-5-thia-1-azabicyclo[4.2.0]oct-2-ene-2-carboxylate-5,5-dioxide with cooling in an ice bath. After stirring for 0.5 hr at 0° C., trifluoroacetic acid was evaporated in vacuo. The residue was diluted with dichloromethane and washed with cold water and brine. The dichloromethane solution was dried over sodium sulfate. Crude 3-acetyloxymethyl-7α-methoxy-8-oxo-5-thia-1-azabicyclo[4.2.0]oct 2-ene-2-carboxylic acid was obtained upon concentration of the filtrate. It was dissolved in 5 ml of tetrahydrofuran and N,N'-diisopropyl-0-benzyl-isourea (0.33 ml, 2.5 mmol) was added. After stirring for 80 hours the reaction mixture wa poured into 7% sodium bicarbonate solution and extracted with ethyl acetate. The combined organic extract was washed with brine and dried over sodium sulfate. The concentrated filtrate was flash chromatographed using 50% ethyl acetate-hexane to yield 259 mg (77% yield) of benzyl 3-acetyloxymethyl-7α-methoxy-8-oxo-5-thia-1-azabicyclo[4.2.0]oct-2-Ⓡn Ⓡ-2-carboxylate as a mixture of Δ2 and Δ3 isomers. NMR(CDCl$_3$): δ 1.96 and 1.98 (s, 3), 3.4 (ABq, 0.8, 17 Hz), 3.43 (s, 1.8), 3.47 (s, 1.2), 4.2–5.3 (m, 6.6), 6.34 (bs, 0.6), 7–7.4 (m, 5).

Following substantially the same Procedure as described in Example 1, Step C, 259 mg (0.69 mmol) of benzyl 3-acetyloxymethyl-7α-methoxy-8-oxo-5-thia-1-azabicyclo[4.2.0]oct-2-ene-2-carboxylate was oxidized to obtain 226 mg (80% yield) of benzyl 3-acetyloxymethyl-7α-methoxy-B-oxo-5-thia-1-azabicyclo[4.2.0]oct-2 ene-2-carboxylate 5,5-dioxide as a thick oil. NMR(CDCl$_3$): δ 2.01 (s, 3), 3.49 (s, 3), 3.8 (ABq, 2, 18 Hz), 4.6 (bs, 1), 4.78 (ABq, 2, 13 Hz), 5.07 (d, 1, 2 Hz), 5.17 (ABq, 2, 11 Hz), 7.1–7.4 (m, 5H).

EXAMPLE 23 t-Butyl 3-acetyloxymethyl-7α-ethyl-8-oxo-5-thia-1-azabicyclo[4.2.0]oct-2-ene-2-carboxylate A 2 liter, 3-necked round bottom flask fitted with 2 dropping funnels was charged with 200 ml THF and cooled to −78° C. under N$_2$. One dropping funnel was charged with a solution of 6.33 g (15.3 mM]t-butyl 3-acetyloxymethyl-7-diazo-8-oxo-5-thia-1-azabicyclo[4.2.0]oct-2-ene-2-carboxylate in 300 ml THF. The other funnel was charged with 32 ml 1M-triethylborane in THF, 1.2 ml H20, and 300 ml THF. The funnels were adjusted so their contents were added to the flask at 2.5 ml/min and the temperature of the reaction mixture maintained at −78°. After the addition, the cooling bath was removed and the reaction mixture allowed to warm. When the temperature reached −45° C., 6.67 ml 30% H$_2$O$_2$ was added. At −15°, the reaction mixture was washed with 300 ml brine, the organic layer diluted with 300 ml CH$_2$Cl$_2$, washed with 300 ml brine, dried over MgSO$_4$, filtered and stripped to give 7.46 g of yellow oil which was chromatographed on a flash column with CHCl$_3$/EtOAc (25:1) to yield 1.289 g (19%) t-butyl-3-acetyl-oxymethyl-7α-ethyl-8-oxo-5-thia-1-azabicyclo[4.2.0]oct-2-ene-2-carboxylate a 4:1 mixture of the α and β isomers NMR(CDCl$_3$): δ 1.08, t (J TM 8Hz), 3H; 1.50, s, 9H; 1.8, br, qt, 2H; 2.05, s, 3H; 3.1, brm, 1H; 3.4, d, 2H; 4.35, d (J=2Hz), 1H; 4.82, AB qt (J=12, 6Hz) 2H.

EXAMPLE 24 t-Butyl 3-acetyloxymethyl-7α-methoxy-4-methyl-8-oxo-5-thia-1-azabicyclo[4.2.0]oct-2-ene-2-carboxylate-5β-oxide Step A: Preparation of t-Butyl 3-acetyloxymethyl-7α-methoxy-4-methylene-8-oxo-5-thia-1-azabicyclo-[4.2.0]oct-2-ene-2-carboxylate-5β-oxide Treatment of t-butyl 3-acetyloxymethyl-7α-methoxy-8-oxo-5-thia-1-azabicyclo[4.2.0]oct 2-ene-2-carboxylate-5β-oxide under Mannich conditions, (i.e., aq. formaldehyde and dimethylamine: HCl in DMF-dioxane) gave t-butyl 3-acetyloxymethyl-7α-methoxy-4-methylene-8-oxo-5-thia-1-azabicyclo[4.2.0]-oct-2-ene-2-carboxylate-5β-oxide as a foam, NMR (CDCl$_3$): δ 1.60 (9H, s), 2.03 (3H, s), 3.57 (3H, s), 4.50 (1H, d, J=1.5Hz), 4.68, 5.30, (2H, ABq, J=13.5Hz), 5.01 (1H, d, J=1.5Hz), 6.33 (2H, s).

Step B: Preparation of t-butyl 3-acetyloxymethyl-7α-methoxy-4-methyl-8-oxo-5-thia-1-azabicyclo [4.2.0]oct-2-ene-2-carboxylate-5β-oxide A solution of the 2-methylene derivative obtained in Step A (178 mg, 0.56 mmol) in ethyl acetate (5 ml) was hydrogenated at atmospheric pressure over an excess of 10% palladium on carton. The catalyst was removed by filtration and the solvent removed by rotoevaporation to give a 1:1 mixture 4α and 4β-methyl isomers of t-butyl 3-acetyloxymethyl-7α-methoxy-4-methyl-8-oxo-5-thia-1-azabicyclo[4.2.0]oct-2-ene-2-carboxylate-5β-oxide (170 mg). The isomers were separated by thick layer preparative chromatography on silica gel eluted with 50% ethyl acetate/hexane (5×). The assignment of the stereochemistry at C-4 was made by Comparing the difference of the chemical shifts in the $^1$H-NMR of the two isomers in CDCl₃ and C₆D₆. The faster moving component was the 4α-methyl isomer oil; NMR (CDCl₃): δ 1.55 (3H, d, J=7.0Hz), 1.57 (9H, s), 2.10 (3H, s), 3.58 (3H, s), 3.88 (1H, q, J=7.0Hz), 4.36 (1H, d, J=1.5Hz), 4.67, 4.87 (2H, ABq, J=13.5Hz), 4.93 (1H, d, J=1.5Hz). The second component was the 4β-isomer: oil; NMR (CDCl₃): δ 1.58 (9H, s), 1.68 (3H, d, J=7.0Hz), 2.06 (3H, s), 3.56 (3H, s), 3.60 (1H, q, J=7.0Hz), 4.48 (1H, d, J=1.5Hz), 4.58, 5.15 (2H, ABq, J=13.4Hz), 4 91 (1H, d J=1.5Hz).

EXAMPLE 25 t-Butyl 3-acetyloxymethyl-7α-methoxy-4-methylene-8-oxo-5-thia-1-azabicyclo[4.2.0]oct-2-ene-2-carboxylate-5,5-dioxide To a stirred solution of t-butyl 3-acetyloxymethyl-7α-methoxy-4-methylene-8-oxo-5-thia-1-azabicyclo[4.2.0]oct-2-ene-2-carboxylate (180 mg, 0.48 mmol) in methylene chloride (2 ml) at 0° C. was added m-chloroperbenzoic acid (109 mg, 0.53 mmol). After stirring the white suspension at room temperature overnight, methylene chloride (25 ml) was added and the solution successively washed with saturated sodium bicarbonate solution (3×10 ml) and water (2×10 ml). After drying over anhydrous sodium sulfate, the solvent was removed by rotoevaporation to give a whitish solid that was purified by flask column chromatography on silica gel eluted with 40% ethyl acetate/hexanes to give 128 mg (69% yield) of t-butyl 3-acetyloxymethyl-7α-methoxy-4-methylene-8-oxo-5-thia-1-aza-bicyclo[4.2.0]oct-2-ene-2-carboxylate-5,5-dioxide m.p. 155°-157° C.; ¹H-NMR (CDCl₃): δ 1.58 (9H, s), 2.03 (3H, s), 3.56 (3H, s), 4.66, 5.30 (2H), ABq, J=13.5 Hz), 4.96 (1H, d, J=1.5 Hz), 5.21 (1H, d, J=1.5 Hz), 6.16 (1H, d, J=1.5 Hz), 6.53 (1H, d, J=1.5 Hz).

EXAMPLE 26 t-Butyl 3-acetyloxymethyl-7α-methoxy-4α-methyl-8-oxo-5-thia-1-azabicyclo[4.2.0]oct-2-ene-2-carboxylate-5,5-dioxide t-Butyl 3-acetyloxymethyl-7α-methoxy-4α-methyl-8-oxo-5-thia-1-azabicyclo[4.2.0]-oct-2-ene-2-carboxylate-5β-oxide was oxidized in the usual manner as described in Example 13 to afford t-butyl 3-acetyloxymethyl-7α-methoxy-4α-methyl-8-oxo-5-thia-1-azabicyclo[4.2.0]oct-2-ene-2-carboxylate-5,5-dioxide as an oil. ¹H-NMR (CDCl₃): δ 1.55 (9H, s), 1.64 (3H, d, J=7Hz), 2.12 (3H, s), 3.56 (3H, s), 3.56 (1H, q, J TM 7Hz), 4.71 (1H, d, J=1.5Hz), 4.70, 4.86 (2H, ABq, J=13.5Hz), 5.16 (1H, d, J=1.5Hz); Field desorption mass spectrum, m/e 389.

Similarly, t-butyl 3-acetyloxymethyl-7α-methoxy-4β-methyl-8-oxo-5-thia-1-azabicyclo[4.2.0]oct-2-ene-2-carboxylate-5β-oxide was oxidized to t-butyl 3-acetyloxymethyl-7α-methoxy-4β-methyl-β-oxo-5-thia-1-azabicyclo[4.2.0]oct-2-ene-2-carboxylate-5,5 dioxide (an oil). ¹H-NMR (CDCl₃): 6 1.55 (9H, s), 1.56 (3H, d, J=7Hz), 2.05 (3H, s), 3.56 (3H, s), 3.96 (1H, q, J-7Hz), 4.56, 5.23 (2H, ABq, J=13.5Hz), 4.78 (1H, d, J=1.5Hz), 5.15 (1H, d, J=1.5Hz); field desorption mass spectrum, m/e 389.

EXAMPLE 27 t-Butyl 3-acetyloxymethyl-7α-methoxy-4-phenylthio-methyl-8-oxo-5-thia-1-azabicyclo[4.2.0]oct-2-ene-2-carboxylate-5,5-dioxide Thiophenol (0.02 ml, 0.15 mmol) was added to a stirred solution of t-butyl 3-acetyloxymethyl-7α-methoxy-4-methylene-8-oxo-5-thia-1-azabicyclo[4.2.0]-oct-2-ene-2-carboxylate-5,5-dioxide (60 mg, 0.15 mmol) in methylene chloride (1 ml). After stirring for 45 minutes, the solvent was removed by rotoevaporation and the residue purified by thick layer preparative chromatography on silica gel eluted with 30% ethyl acetate/hexanes to afford t-butyl 3-acetyloxymethyl-7α-methoxy-4-phenylthiomethyl-8-oxo-5-thia-1-azabicyclo[4.2.0]oct-2-ene-2-carboxylate- 5,5-dioxide as a pale yellow oil (38 mg, 50% yield): ¹H-NMR(CDCl₃): δ 1.53 (9H, s), 2.00 (3H, s), 3.33 (1H, dd, J=15 and 9Hz), 3.51 (3H, s), 3.57 (1H, d, J=15Hz), 3.80 (1H, m), 4.21, 4.40 (2H, ABq, J=12Hz), 5.10 (2H, br s); field desorption mass spectrum, m/e 497.

EXAMPLE 28 t-Butyl 7α-methoxy-3-[[(1,2,5,6-tetrahydro-5'6-dioxo-2-methyl-as-triazin-3-yl)thio]methyl]-8-oxo-5-thia-1-azabicyclo[4.2.0]-oct-2-ene-2-carboxylate-5,5-dioxide A solution of 32 mg (0.2 mmol) of 1,2,5,6-tetrahydro-5,6-dioxo-3-mercapto-2-methyl-astriazine in 1 ml of water was prepared by adding 35 mg (0.42 mmol) of NaHCO₃. A solution of 70 mg (0.2 mmol) of t-butyl 3-chloromethyl-7α-methoxy-8-oxo-5-thia-1-azabicyclo[4.2.0]-oct-2-ene-2-carboxylate-5,5-dioxide in 2 ml of acetone was added. After stirring the reaction mixture overnight it was concentrated in vacuo. The residue was partitioned between 7% NaHCO₃ and ether. The ether layer was extracted with 7% NaHCO₃ solution. The combined aqueous layer was washed with ether. The aqueous layer was acidified to pH 2 in the presence of ethyl acetate using concentrated HCl. The layers were separated and the aqueous layer was extracted with ethyl acetate. The combined organic layer was washed with saturated NaCl and dried. The filtrate was concentrated and the residue was crystallized from ethyl acetate and ether. t-Butyl 7α-methoxy-3-[[(1,2,5,6-tetrahydro-5,6-dioxo-2-methyl-as-triazin-3-yl)thio]methyl]-8-oxo-5-thia-1-azabicyclo[4.2.0]-oct-2-ene-2-carboxylate-5,5-dioxide (76 mg, 80% yield) was obtained as a light yellow solid. HNMR (CDCl₃): δ 1.58 (s, 9H), 3.58 (s, 3), 3.77 (s, 3H), 3.8–4.5 (m, 5H), 4.74 (bs, 1H), 5.18 (bs, 1H).

EXAMPLE 29 t-Butyl 7α-methoxy-3[[(1-carboxymethyl-tetrazol-5-yl)-thio[-methyl]-8-oxo-5-thia-1-azabicyclo[4.2.0]oct-2-ene-2-carboxylate-5,5-dioxide A solution of 32 mg (0.2 mmol) of 1-carboxymethyl-5-mercaptotetrazole in 1 ml of water was prepared by adding 35 mg (0.42 mmol) of NaHCO₃. A solution of 70 mg (0.2 mmol) of t-butyl 3-chloromethyl-7α-methoxy-8-oxo-5-thia-1-azabicyclo[4.2.0]-oct-2-ene-2-carboxylate-5,5-dioxide in 2 ml of acetone was added. After stirring the reaction mixture overnight it was concentrated in vacuo. The residue was partitioned between 7% NaHCO$_3$ solution and ether. The aqueous layer was neutralized with concentrated HCl in the presence of ethyl acetate. The layers were separated and the aqueous layer was extracted with ethyl acetate. The combined organic layer was washed with saturated NaCl and dried The filtrate was concentrated and the residue was triturated with ether to obtain 70 mg (73% yield) of t-Butyl 7α-methoxy-3[[(1-carboxymethyl-tetrazol-5-yl)-thio]methyl]-8-oxo-5-thia-1-azabicyclo[4.2.0]oct-2-ene-2-carboxylate-5,5-dioxide as a white powder.

HNMR (CDCl$_3$): δ 1.58 (s, 9H), 3.56 (s, 3H), 3.87 (d, J=17 Hz, 1M), 4.05 (d, J=13 Hz, 1H) 4.2 (d, J=17 Hz, 1H), 4.6 (d, J=13 Hz, 1H), 4.75 (s, 1H), 5.16 1 (ABq, J=16 Hz, 2H), 5.16 (bs, 1M), 6.9 (broad, 1H).

EXAMPLE 30

N-Methyl-N-t-butoxycarbonylmethyl-3-chloromethyl-7α-methoxy-8-oxo-5-thia-1-azabicyclo[4.2.0]-oct-2-ene-2-carboxylate-5,5-dioxide To a solution of 2.6 g (5.8 mmol) of N-methyl-N-t-butoxycarbonylmethyl-3-acetyloxymethyl-7α-methoxy-8-oxo-5-thia-1-azabicyclo[4.2.0]-oct-2-ene-2-carboxamide-5,5-dioxide in 13 ml of 2-propanol was added 1.95 ml (6.5 mmol) of titanium (IV) isopropoxide. The solution was heated in a 55° bath. After 1.5 hours the orange reaction mixture was diluted with ethyl acetate and poured into water. The layers were separated and the aqueous layer was extracted with ethyl acetate. The combined organic layer was washed with water, saturated NaCl and dried. The filtrate was concentrated in vacuo to obtain 2.06 g of residue.

The residue was dissolved in 20 ml of tetrahydrofuran and 1.75 ml of pyridine. The solution was cooled in an ice-bath and 0.58 ml (7.4 l mmol) of thionyl chloride was added. After stirring for 20 minutes the dark reaction mixture was diluted with ethyl acetate and poured into water. The layers were separated and the aqueous layer was extracted with ethyl acetate. The combined organic layer was washed with 7% NaHCO$_3$, water, 1.2N HCl, saturated NaCl and dried. The filtrate was concentrated. The residue was chromatographed on a flash column using 60% ethyl acetate-hexane to obtain 710 mg (29% yield) of N-methyl-N-t-butoxycarbonylmethyl-3-chloromethyl-7α-methoxy-8-oxo-5-thia-1-azabicyclo[4.2.0]-oct-2-ene-2-carboxamide-5,5-dioxide.

$^1$H NMR (CDCl$_3$): δ 1.48 and 1.52 (2s, 9H), 3.1 and 3.12 (2s, 3H), 3.39 and 3.57 (2s, 3H), 3.6–4.8 (m, 6H), 4.92 (bs, 1H), 5.25 (d, J=2 Hz, 1H).

EXAMPLE 31

N-Methyl-N-t-butoxycarbonylmethyl-7α-methoxy-3[[(1,2, 5,6-tetrahydro-5,6-dioxo-2-methyl-as-triazin-3-yl) thio]methyl]-8-oxo-5-thia-1-azabicyclo[4.2.0]-oct-2-ene-2-carboxamide-5,5-dioxide A solution of 53 mg (0.33 mmol) of 1,2,5,6-tetrahydro-5,6-dioxo-3-mercapto-2-methyl-as-triazine in 1 ml of water was prepared by adding 57 mg (0.68 mmol) of NaHCO$_3$. A solution of 140 mg (0.33 mmol) of N-methyl-N-t-butoxycarbonylmethyl-3-chloromethyl-7α-methoxy-8-oxo-5-thia-1-azabicyclo[4.2.0]-oct-2-ene-2-carboxamide-5,5-dioxide in 2 ml of water was added. After stirring the reaction mixture overnight it was concentrated in vacuo. The residue was partitioned between 1% NaHCO$_3$ and ether. The aqueous layer was acidified with concentrated HCl in the presence of ethyl acetate. The layers were separated and the aqueous layer was extracted with ethyl acetate. The combined organic layer was washed with saturated NaCl and dried. The filtrate was concentrated and the residue was triturated with ether to obtain 110 mg (60% yield) of N-methyl-N-t-butoxycarbonylmethyl-7α-methoxy-3[[(1,2, 5,6-tetrahydro-5,6-dioxo-2-methyl-as-triazin-3-yl) thio]methyl]-8-oxo-5-thia-1-azabicyclo[4 2.0]-oct-2-ene-2-carboxamide-5,5-dioxideas a white solid.

$^1$HNMR (Aceton-d$_6$): δ 1.48 (s, 9H), 3.06 (broad, 1H), 3.15 (s, 3H), 3.55 and 3.56 (2s, 3H), 3.73 and 3.75 (2s, 3H), 3.9–4.5 (m, 6H), 5.26 (s, 1H), 5.38 (s, 1H).

EXAMPLE 32

3-Acetoxymethyl-7α-methoxy-8-oxo-5-thia-1-aza-bicyclo [4.2.0]-oct-2-ene-2-morpholino carboxamide

Step A: Preparation of 3-acetoxymethyl-7α-methoxy-8-oxo-5-thia-1-aza-bicyclo[4.2.0]-oct-3-ene-2-morpholino carboxamide To a solution of 3-acetoxymethyl-7-methoxy-8-oxo-5-thia-1-azabicyclo[4.2.0]-oct-2-ene-2-carboxylic acid (5.0 g) in dioxane (50 ml) were added N-hydroxysuccinimide (2.4 g) and dicylohexyl carbodiimide (5.4 g). After stirring for 0.5 hour, the reaction was cooled to 5° C. and triethylamine (4 mL) and, after another 15 minutes, morpholine (3.0 g) were added. After 1.5 hours stirring at room temperature, the reaction was diluted with diethyl ether, filtered and washed with water containing 40 mL of 2N HCl. The aqueous layer was extracted with ethyl acetate (3×) and each layer was consecutively washed with water and brine. The combined organic layers were dried over sodium sulfate and evaporated and the residue flash chromatographed (60 to 70% ethyl acetate/hexanes) to give 2.0 g of 3-acetoxymethyl-7α-methoxy-8-oxo-5-thia-1-aza-bicyclo [4.2.0]-oct-3-ene-2-morpholino carboxamide. NMR (CDCl$_3$): δ 2.08 (s, 3H), 3.54 (s, 3H), 3.6–3.9 (m, 8H), 4.57 (AB quartet, 2H), 4.60 (br s, 1H), 4.92 (s, 1H), 5.32 (br s, 1H), 6.54 (br s, 1H).

Step B: Preparation of 3-Acetoxymethyl-7α-methoxy-8-oxo-5-thia-1-azabicyclo[4.2.0]-oct-2-ene-2-morpholino carboxamide A solution of 3-acetoxymethyl-7α-methoxy-8-oxo-5-thia-1-azabicyclo[4.2.0]-oct-3-ene-2-morpholino carboxamide (2.0 g) and m-chloroperbenzoic acid (3.4 g) in methylene chloride (100 mL) was stirred at room temperature for 16 hours. Amberlyst A-21 resin (17 g) was then added and, after 0.5 hours, the mixture was filtered and evaporated. Flash chromatography (70% ethyl acetate/hexanes) of the residue afforded 1.85 g of 3-acetoxymethyl-7α-methoxy-8-oxo-5-thia-1-azabicyclo[4.2.0]-oct-2-ene-2-morpholino carboxamide-5,5-dioxide.

NMR (CDCl$_3$): δ 6 2.13 (s, 3H), 3.4–4.1 (m, 10H), 3.58 (s, 3H), 4.57 (ABq, 2H), 4.82 (br s, 1H), 5.23 (d, 1H, J=1 Hz).

EXAMPLE 33

3-Acetoxymethyl-7α-methoxy-8-oxo-5-thia-1-azabicyclo[4.2.0]-oct-2-ene-2-(2-(S)-carboxypyrrolidinocarboxamide)-5,5-dioxide

Step A: Preparation of t-butyl 3-acetoxymethyl-7α-methoxy-8-oxo-5-thia-1-azabicyclo[4.2.0]-oct-3-ene-2-(2-(S)-carboxypyrrolidinocarboxamide)

To a solution of 3-acetoxymethyl-7-methoxy-2-cephem-4-carboxylic acid (7.4 g) in dioxane (100 ml) was added N-hydroxysuccinimide (3.5 g) followed by dicyclohexylcarbodiimide (7.9 g). After 0.5 hour at room temperature, the reaction was cooled to 5° C. and triethylamine (7.1 mL) was added. After 15 minutes, L-proline t-butyl ester (6.6 g) was added. After 1.5 hour at room temperature, the reaction was diluted with ether, filtered and washed with dilute hydrochloric acid. The aqueous layer was extracted with another 2 portions of ethyl acetate and each organic layer was washed with water 2% sodium bicarbonate solution and brine. The combined organic layers were dried over sodium sulfate and evaporated. The residue on flash chromatography (40% ethyl acetate/hexanes) gave 0.80 g of t-butyl 3-acetoxymethyl-7α-methoxy-8-oxo-5-thia-1-azabicyclo[4.2.0]-oct-3-ene-2-(2-(S)-carboxypyrrolidinocarboxamide). NMR (CDCl$_3$): δ 1.45 and 1.52 (2s, 9H), 2.08 and 2.08 (2s, 3H), 1.8–2.4 (m, 4H), 3.52 and 3.54 (2s, 3H), 3.75 (m, 1H), 4.05 (m, 1H), 4.4 (m, 1H), 4.60 (ABq, 2H), 4.66 (br s, 1H), 4.96 (br s, 1H), 5.20 (br s, 1H), 6.44 and 6.46 (2 br s, 1H).

The above sodium bicarbonate wash was acidified with 2N hydrochloric acid in the presence of ethyl acetate and the ethyl acetate layer was washed with brine, dried over sodium sulfate and evaporated to give 3.4 g of essentially pure 3-acetoxymethyl-7α-methoxy-8-oxo-5-thia-1-azabicyclo [4.2.0]-oct-3-ene-2-carboxylic acid.

NMR (CDCl$_3$): δ 6 2.10 (s, 3H), 3.58 (s, 3H), 4.50 (s, 1H), 4.55 (ABq, 2H), 5.06 (s, 1H), 5.10 (br s, 1H), 6.51 (br s, 1H), 7.06 (br s, 1H).

Step A: (Alternate) Preparation of t-butyl 3-acetoxy-methyl-7α-methoxy-8-oxo-5-thia-1-azabicyclo[4.2.0]-oct-3-ene-2-(2-(S)-carboxypyrrolidinocarboxamide To a solution of 3-acetoxymethyl-7α-methoxy-8-oxo-5-thia-1-azabicyclo[4.2.0]-oct-3-ene-2-carboxylic acid (0.5 g) in dioxane (20 mL) at 5° C. was added dicyclohexylcarbodiimide (0.71 g), followed after 10 minutes by slow addition of L-proline t-butyl ester (0.30 g) in 5 mL of dioxane over 5 minutes The reaction was stirred at room temperature for 24 hours before being diluted with ether, filtered and washed with dilute hydrochloric acid. The aqueous layer was extracted with 3 portions of ethyl acetate and each organic layer consecutively was washed with water and brine. The combined organic layers were dried over sodium sulfate and evaporated. The residue on flash chromatography (40% ethyl acetate/hexanes) afforded 450 mg of t-butyl 3-acetoxymethyl-7α-methoxy-8-oxo-5-thia-1-azabicyclo[4 2 0]-oct-3-ene-2-(2-(S)-carboxypyrrolidinocarboxamide. NMR was same as above.

Step B: Preparation of t-butyl 3-acetoxymethyl-7α-methoxy-8-oxo-5-thia-1-azabicyclo[4.2.0]-oct-2-ene-2-(2-(S)-carboxypyrrolidinocarboxamide)-5,5-dioxide A solution of t-butyl 3-acetoxymethyl-7α-methoxy-7α-methoxy-8-oxo-5-thia-1-azabicyclo [4.2.0]-oct-3-ene-2-(2-(5)-carboxypyrrolidinocarboxamide) (3.1 g) and m-chloroperbenzoic acid (4.7 g) in methylene chloride (150 mL) was stirred at room temperature for 16 hours. The reaction was then poured into a solution of sodium bicarbonate and sodium sulfite and the layers separated The organic layer was washed with brine, dried over sodium sulfate and evaporated after addition of 5 drops of pyridine The residue on flash chromatography (40–60% ethyl acetate/hexanes) afforded 2 8 g of 3-acetoxymethyl-7α-methoxy-8-oxo-5-thia-1-azabicyclo-[4.2.0]-oct-2-ene-2-(2-(S)-carboxypyrrolidinocarboxamide)-5,5-dioxide t-butyl ester. NMR (CDCl$_3$): δ 1.40 and 1.44 (2s, 9H), 2.01 and 2.03 (2s, 3H), 1.8–2.4 (m, 4H), 3.4–3.7 (m, 2H), 3.49 and 3.52 (2s, 3H), 3.80 (ABq, 2H), 4.17 and 4.38 (2 dd, 1H, J=8 Hz, J=2 Hz), 4.5–4.8 (2 ABq, 2H), 4.80 and 4.85 (2 br s, 1H), 4.84 (2d, 1H, J=2Hz).

Step C: Preparation of 3-acetoxymethyl-7α-methoxy-8-oxo-5-thia-1-azabicyclo[4.2.0]-oct-2-ene-2-(2-(S)-carboxypyrrolidinocarboxamide)-5,5-αdioxide t-Butyl 3-acetoxymethyl-7α-methoxy-8-oxo-5-thia-1-azabicyclo[4.2.0]-oct-2-ene-2-(2-(S)-carboxypyrrolidinocarboxamide)-5,5-dioxane (400 mg) was taken up in 1 mL of anisole and 15 mL of TFA (precooled to 0° C.) and stirred in an ice bath for ½ hour. Most of the TFA/anisole was removed in vacuo and then under a stream of N$_2$. The residue was eluted on 2×2000 μm silica prep plates (1% HOAc in ethyl acetate) to give 250 mg of 3-acetoxymethyl-7α-methoxy-8-oxo-5-thia-1-azabicyclo[4.2.0]-oct-2-ene-2-(2-(S)-carboxypyrrolidinecarboxamide)-5,5-dioxide.

NMR (CDCl$_3$): δ 6 2.08 and 2.11 (2s, 3H), 1.8–2.4 (m, 4H), 3.56 and 3.60 (2s, 3H), 3.4–4.0 (m, 2H), 3.90 (ABq, 2H), 4.4–5.0 (m, 3H), 4.90 (br s, 1H), 4.26 (br s, 1H).

EXAMPLE 34

Step A: Preparation of t-butyl 3-acetyloxymethyl 7β-amino-8-oxo-5-thia-1-azabicyclo[4.2.0]oct-3-ene-2-carboxylate (t-butyl 7-ACA, 2)

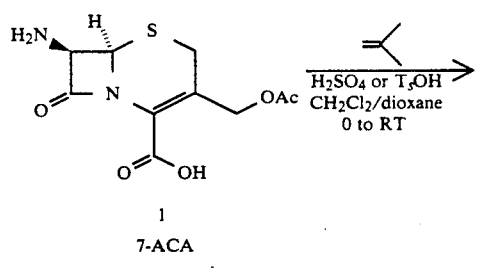

1
7-ACA

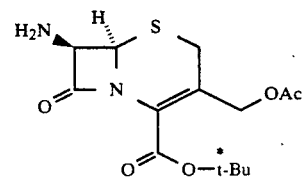

2

*t-Bu can be substituted by another protecting group, e.g., $C_{1-6}$ alkyl; benzhydryl, benzyl and the like.

A suspension of tosic acid monohydrate (500 gms, 2.6 moles) in toluene (2L) was dehydrated by refluxing under a Dean-Stark trap for 40 hrs. At this time all of the tosic acid had gone into solution and a total of 57 mL of water had been collected. The toluene was then removed in vacuo to afford a colored, solid mass.

The dehydrated tosic acid was taken up in methylene chloride (2500 mL) and transferred to a 5-L 3-necked round bottom flask which had been fitted with a mechanical stirrer, $N_2$ and gas inlet tubes and a dry ice condenser Solid 7-ACA (1) (355 gms, 1.3 moles) was slowly added at a rate to achieve solution of the 7-ACA without formation of a gummy mass. The solution was then cooled to 10°-15° C. and isobutylene (1000 mL) was distilled into the reaction mixture over 2½ hrs. Note: Rapid addition of the isobutylene causes formation of a gummy precipitate. The reaction mixture was stirred overnight at room temperature.

The reaction was slowly quenched with vigorous stirring into a 5-gallon carboy containing a solution of sodium bicarbonate (500 gms) in ice water (6L). The organic layer was separated using suction and washed with water and brine. The aqueous layers were sequentially back-extracted with two portions of methylene chloride (500 mL) and the combined layers were dried over sodium sulfate. Most of the methylene chloride was removed in vacuo until the product began to solidify. At this time cyclohexane (1L) was added and the precipitate was triturated to break up the clumps. The product was collected by filtration, washed with cyclohexane and dried overnight by pulling air through the filter cake. The yield of t-butyl 7-ACA (2) was 360 grms (80%) as an off-white solid. $R_f(Et_2O) = 0.3-0.5$.

Step B: Preparation of t-butyl-3-acetyloxymethyl-7α-methoxy-8-oxo-5-thia-1-azabicyclo[4.2.0]oct-3-ene-2-carboxylate (3)

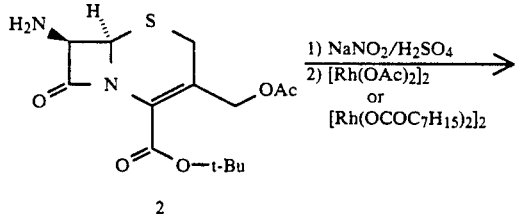

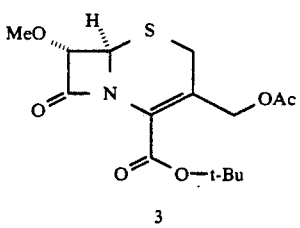

The diazotization reaction was run in two 50 gm batches and then combined for the work-up and second step.

To duplicate solutions of t-butyl 7-ACA 2 (2×50 gms, 0.30 moles) in methylene chloride (2×600 mL) was added sodium nitrite (2×11.4 g, 0.33 moles) dissolved in water (2 x 500 mL). The mixtures were cooled in an ice bath and to each was added 2N $H_2SO_4$ (2×114 mL, 0.450 moles) in portions over five minutes and the reactions were stirred for 45 minutes at 0° C. They were then combined and the organic layer was separated (some problems with emulsions) and washed with water and brine. The aqueous layers were back-extracted with methylene chloride and the organic layers combined, dried over sodium sulfate and filtered.

To the above methylene chloride solution was added at room temperature methanol (800 mL) and, while vigorously stirring, rhodium acetate dimer (0.64 gms). Vigorous nitrogen evolution occurred and after ½ hr the reaction was filtered through celite and concentrated in vacuo at low temperature. The residue was taken up in ether and washed with water and brine to remove any residual methanol. The aqueous layers were back-extracted with ether and the organic layers were combined, dried over sodium sulfate and evaporated in vacuo. The residue was purified by preparative HPLC in two portions using 15% EtOAc/hexane as eluent. The yield of 3 was 25-30 gms (25%) as a yellow oil which slowly crystallized on standing. $R_f$ (25% EtOAc/hex) = 0.50. The product 3 was the first major component on TLC.

Step C: Preparation of 3-acetyloxymethyl-7α-methoxy-8-oxo-5-thia-1-azabicyclo[4.2.0]oct-3-ene-2-carboxylic acid (4)

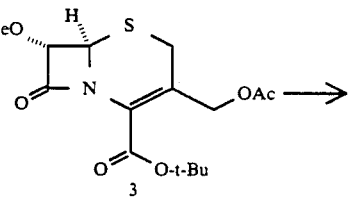

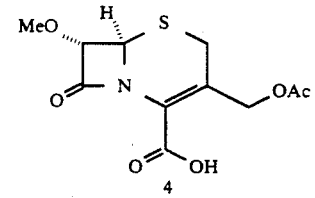

To a solution of TFA (75 mL) and anisole (5 mL) at 0° was added the t-butyl sulfide 3 (18 gms) as a solid or in a minimum amount of methylene chloride. The reaction was stirred at 0° for 1 hr or until it was judged nearly complete by TLC (Note: The reaction never seems to go to completion). The solution was then poured into a mixture of ice water (200 mL) and methylene chloride (200 mL) and the organic layer was separated and washed twice with water (100 mL). Each aqueous layer was sequentially back extracted with an additional three portions of methylene chloride (200 mL). The combined methylene chloride layers were extracted twice with water containing enough sodium bicarbonate solution to maintain the pH at 7-8 and each extract was washed with methylene chloride. The combined aqueous layers were acidified with 2N hydrochloric acid in the presence of ethyl acetate. The layers were separated and the organic layer was washed with brine. The aqueous layers were back extracted with three portions of ethyl acetate (50 mL) and these were combined, dried over sodium sulfate and evaporated. The crude product 4 was usually a dark, sticky foam and was used as obtained as soon as possible. The yield of 4 was typically 12-14 gms (80-90%).

Step D: Preparation of N-benzoxycarbonyl-L-Proline (6)

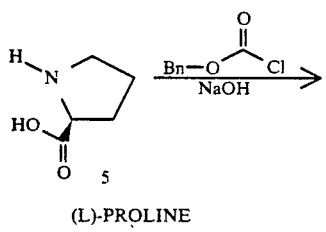

(L)-PROLINE

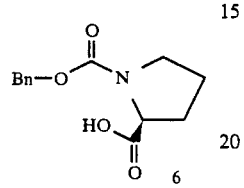

L-Proline 5 (100 gms, 0.87 moles) was dissolved in 2N sodium hydroxide (430 mL) and cooled in an ice bath. A further 220 mL of 4N sodium hydroxide was added simultaneously with benzyl chloroformate (155 gms, 0.90 moles) over 2 hrs. The reaction was then allowed to warm to room temperature overnight.

The reaction was washed twice with ether (500 mL) and the aqueous layer acidified with concentrated hydrochloric acid and extracted twice with ethyl acetate (500 mL). The combined organic layers were washed with brine and dried over sodium sulfate. Evaporation in vacuo gave 268 gms of crude 6 as a thick oil. This was used directly in the next reaction.

Step E: Preparation of t-butyl N-benzoxycarbonylpyrrolidine-=2-carboxylate (7)

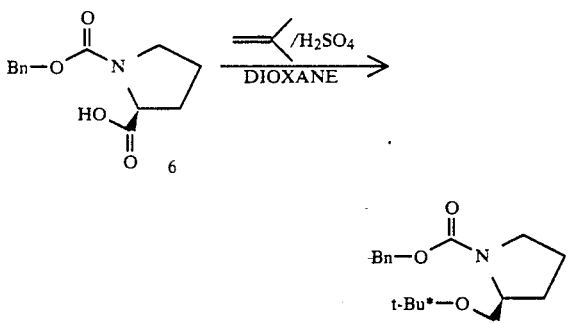

*t-Bu can be substituted by a protecting group such as $C_{1-6}$ alkyl, benzyl, benzhydryl and the like.

The above product 6 was taken up in dioxane (1400 mL) and placed in two 2-L Pressure bottles. To each bottle was added conc. sulfuric acid (30 mL) and condensed (dry ice bath) isobutylene (350 mL).

The bottles were stoppered, fastened with wire and the reactions were stirred at room temperature overnight. The reactions became homogeneous after approximately 1 hr.

The solutions were cooled (until dioxane started to freeze), carefully vented and poured into a carboy containing a solution of sodium bicarbonate (250 gms) in ice water (4 L) and ether (2L). The layers were separated and the ether was washed with water and brine. The aqueous layers were back-extracted with ether and the ether layers were combined and dried over sodium sulfate. Evaporation in vacuo gave 185 gms of crude 7 as a clear oil. This was used directly in the next step.

Step F: Preparation of t-butyl pyrrolidine-2-carboxylate (8)

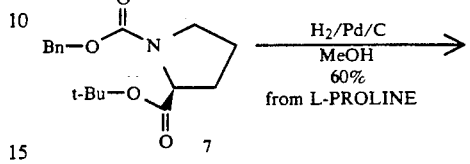

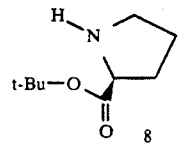

The above oil 7 was taken up in methanol (1500 mL) and hydrogenated over 10% pd/C (8 gms) for 20 hrs. (left overnight for convenience). The reaction was filtered and concentrated in vacuo without heating. The residue was distilled at 55°-65° C./ 1 torr to give 85 gms (60% overall from L-proline) of t-butyl L-proline (8).

Step G: Preparation of 3-acetyloxymethyl-7α-methoxy-8-oxo-5-thia-1-azabicyclo[4.2.0]oct-2-ene-2-(2-(s)-carboxypyrrolidinecarboxamide) (9)

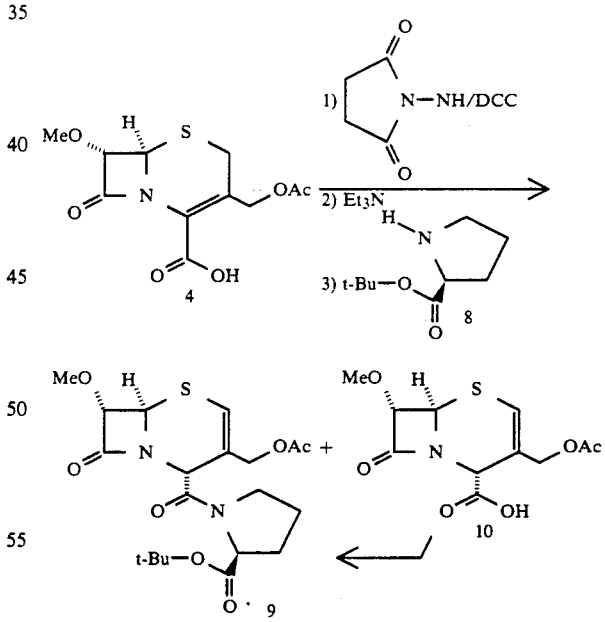

To an ice bath cooled solution of the crude acid 4 (11.5 gms, 40 mmoles) in dioxane (100 mL) are sequentially added N-hydroxysuccinimide (5.7 gms, 50 mmole) and DCC (12.4 gms, 60 mmoles). The reaction was then stirred under nitrogen at room temperature for ½ hr during which time a thick precipitate formed. The reaction was again cooled in an ice bath before dry triethylamine (5.5 mL, 40 mmoles) was added and the stirring was continued for another ½ hr. Finally, t-butyl L-proline 8 (14 gms, 80 mmole) was added all at once. After a further 2 hrs at room temperature, the reaction was diluted with ether (200 mL), filtered, and quenched into ice water (200 mL) containing 60 mL of 2N hydrochloric acid. The layers were separated and the organic layer was washed with water, sodium bicarbonate solution and brine. Each aqueous layer was back extracted with another 100 mL of ether. The organic layers were combined, dried over sodium sulfate and evaporated in vacuo. The product 9 was purified by preparative HPL (45%) EtOAc/hexanes to give 10.5 gms (60%) of 9 as a slightly colored oil. The product 9 was usually accompanied by a small amount of $\Delta^3$ Product as well as some DCC by-product.

The above sodium bicarbonate wash of was acidified in the presence of EtOAc to a pH of 1-2 layers were separated. The aqueous layer was re-extracted with another two portions of ethyl acetate and the organic layers were combined, dried over sodium sulfate and evaporated to give 0.5-2.0 gms of recovered $\Delta^2$ acid 10. This was readily recycled similar to the above reaction to obtain 9.

Step H: Preparation of t-butyl 3-acetoxymethyl-7α-methoxy-8-oxo-5-thia-1-azabicyclo[4.2.0.]oct-2-ene-2-(2-(s)-carboxypyrrolidine carboxamide)-5,5-dioxide (11)

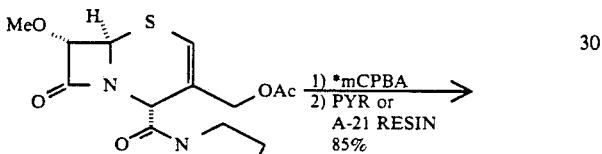

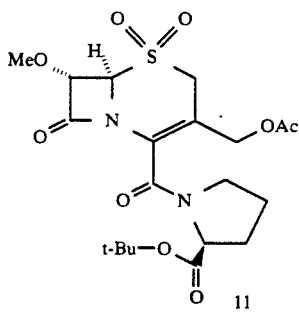

To a solution of $\Delta^2$-sulfide 9 (10.5 gms, 24 mmole) in methylene chloride (700 mL) (Note: The reaction should be kept dilute to avoid any problem with t-Bu ester loss) was added 85 m-chloroperbenzoic acid (14.7 gms, 72 mmole). The solution was stirred at room temperature overnight. The reaction was then quenched into a mixture of sodium bicarbonate and excess sodium sulfite. The layers were separated and the organic layer was washed with brine containing a few milliliters of saturated sodium sulfite solution. The aqueous layers were back extracted with methylene chloride and the organic layers were combined and dried over sodium sulfate. Pyridine (5 drops) or amberlyst A-21 resin (5-10 gms) were added and the mixture stirred for ½ hr in order to completely isomerize the product to $\Delta^3$. Filtration (for A-21 resin) and evaporation gave a crude residue which was Purified by preparative HPLC (50% EtOAc/hexanes) to give 9.5 gms (85%) of 11 as a white foam.

Step I: Preparation of 3-acetyloxymethyl-7α-methoxy-8-oxo-5-thia-1-azabicyclo[4.2.0]oct-2-ene-2-(2-(s)-carboxypyrrolidinecarboxamide)-5,5-dioxide (compound A)

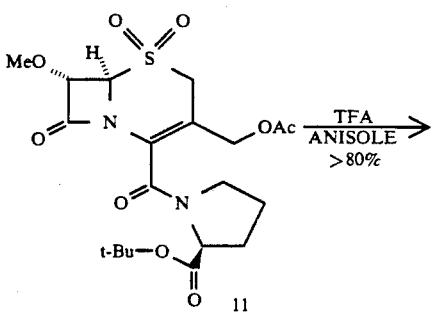

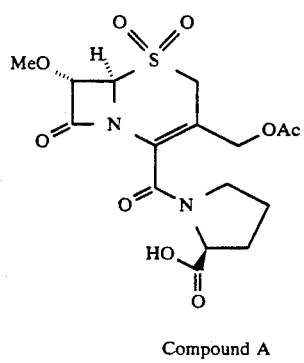

Compound A

To an ice bath cooled solution of TFA (75 mL) and anisole (5 mL) was added the t-butyl sulfone 11 (8.0 gms). After stirring for 1 hr at 0° C., the reaction was evaporated in vacuo without much heating. The residue was taken up in methylene chloride and re-evaporated to remove most of the TFA. The remaining volatiles were blown off in a stream of nitrogen and the product was precipitated and triturated with ether and filtered. The product was redissolved in a minimum amount of methylene chloride and reprecipitated with ether to give 6.4 gms of off-white solid. The combined mother liquors were evaporated and the residue was flash chromatographed eluting with a solvent gradient of 60% EtOAc/hexane to 80% EtOAc/hexane and finally 1% HOAc/EtOAc to give 950 mg of pure compound A after evaporation of 50 mL of toluene to remove any residual acetic acid.

The 6.4 gms were flash chromatographed as above in 3 portions, obtaining 1.86 gms of compound A from a 2.0 gm portion. NMR (CDCl$_3$): δ2.08 and 2.11 (2s, 3H); 1.8-2.4 (m, 4H); 3.56 and 3.6 (2s, 3H); 3.4-4.0 (m, 2H); 3 90 (ABq, 2H); 4.4-5.0 (m, 3H); 4.90 (brs, 1H); 4.26 (brs, 1H).

What is claimed is:
1. A compound which is:
   3-acetyloxymethyl-7α-methoxy-8-oxo-5-thia-1-azabicyclo[4.2.0]oct-2-ene-2-(2-(S)-carboxypyrrolidine-carboxamide)-5,5-oxide.
2. A compound which is:
   p-hydroxycarbonylbenzyl 3-acetyloxymethyl-7α-methoxy-8-oxo-5-thia-1-azabicyclo[4.2.0]oct-2-ene-2-carboxylate.
3. A compound which is:

m-methoxycarbonylbenzyl 3-acetyloxymethyl-7α-methoxy-8-oxo-5-thia-1-azabicyclo[4.2.0]oct-2-ene-2-carboxylate-5,5-oxide.

4. A pharmaceutical composition for treating elastase-mediated diseases comprising a pharmaceutically acceptable salt and a non-toxic effective amount of 3-acetyloxymethyl-7α-methoxy-8-oxo-5-thia-1-azabicyclo[4.2.0]oct-2-ene-2-(2-(S)-carboxypyrrolidine-carboxamide)-5,5-oxide.

5. A pharmaceutical composition for treating elastase-mediated diseases comprising a pharmaceutically acceptable salt and a non-toxic effective amount of p-hydroxycarbonylbenzyl 3-acetyloxymethyl-7α-methoxy-8-oxo-5-thia-1-azabicyclo[4.2.0]oct-2-ene-2-carboxylate.

6. A pharmaceutical composition for treating elastase-mediated diseases comprising a pharmaceutically acceptable salt and a non-toxic effective amount of m-methoxycarbonylbenzyl 3-acetyloxymethyl-7α-methoxy-8-oxo-5-thia-1-azabicyclo[4.2.0]oct-2-ene-2-carboxylate-5,5-oxide.

* * * * *